United States Patent
Sakurada et al.

(10) Patent No.: US 11,026,572 B2
(45) Date of Patent: Jun. 8, 2021

(54) OPHTHALMIC EXAMINATION SYSTEM AND OPHTHALMIC EXAMINATION MANAGEMENT SERVER

(71) Applicant: TOPCON CORPORATION, Itabashi-ku (JP)

(72) Inventors: Tomohiro Sakurada, Itabashi-ku (JP); Yukio Ikezawa, Itabashi-ku (JP)

(73) Assignee: TOPCON CORPORATION, Tokyo (JP)

( * ) Notice: Subject to any disclaimer, the term of this patent is extended or adjusted under 35 U.S.C. 154(b) by 287 days.

(21) Appl. No.: 15/404,552

(22) Filed: Jan. 12, 2017

(65) Prior Publication Data
US 2017/0215723 A1    Aug. 3, 2017

(30) Foreign Application Priority Data
Feb. 1, 2016   (JP) .............................. JP2016-017381

(51) Int. Cl.
*A61B 3/032*    (2006.01)
*A61B 3/00*    (2006.01)
*A61B 3/10*    (2006.01)

(52) U.S. Cl.
CPC ............ *A61B 3/032* (2013.01); *A61B 3/0025* (2013.01); *A61B 3/0033* (2013.01); *A61B 3/0041* (2013.01); *A61B 3/10* (2013.01)

(58) Field of Classification Search
CPC ... A61B 3/0025; A61B 3/0033; A61B 3/0041; A61B 3/032; A61B 3/10
See application file for complete search history.

(56) References Cited

U.S. PATENT DOCUMENTS

2002/0080329 A1    6/2002  Kasahara
2005/0012896 A1    1/2005  Fukuma et al.
(Continued)

FOREIGN PATENT DOCUMENTS

CN    104856642 A    8/2015
JP    2000-102514 A    4/2000
(Continued)

OTHER PUBLICATIONS

Office Action dated Oct. 1, 2019, issued in corresponding Japanese Patent Application No. 2016-017381, 13 pages with English Translation.
(Continued)

*Primary Examiner* — Gil H. Lee
(74) *Attorney, Agent, or Firm* — Xsensus LLP

(57) ABSTRACT

In an ophthalmic examination system of one embodiment, an internal examiner terminal is used by an internal examiner in a facility where an ophthalmic examination apparatus is installed. An external examiner terminal is used by an external examiner outside the facility. A management apparatus includes a communication establishment unit, and an information transfer unit. The communication establishment unit is capable of establishing communication between at least two apparatuses selected from the ophthalmic examination apparatus, the internal examiner terminal, and the external examiner terminal. The information transfer unit is configured to transfer information sent from one of the at least two apparatuses whose communication has been established by the communication establishment unit. Each of the ophthalmic examination apparatus, the internal examiner terminal, and the external examiner terminal includes an output unit configured to output information transferred by the information transfer unit.

12 Claims, 13 Drawing Sheets

(56) References Cited

U.S. PATENT DOCUMENTS

| | | | |
|---|---|---|---|
| 2005/0264760 A1* | 12/2005 | Ikezawa | A61B 3/032 351/239 |
| 2010/0278398 A1* | 11/2010 | Karnowski | G06F 19/321 382/128 |
| 2013/0331664 A1 | 12/2013 | Gilad-Gilor | |
| 2013/0338447 A1 | 12/2013 | Gilad-Gilor | |
| 2014/0073880 A1 | 3/2014 | Boucher et al. | |
| 2014/0129259 A1* | 5/2014 | Seriani | G06F 19/3418 705/3 |
| 2014/0300860 A1* | 10/2014 | Tanaka | A61B 3/18 351/205 |
| 2015/0042951 A1 | 2/2015 | Stange et al. | |
| 2015/0070650 A1* | 3/2015 | Seriani | A61B 3/0025 351/204 |
| 2016/0103966 A1 | 4/2016 | Mirza | |
| 2016/0124249 A1 | 5/2016 | Haddadi et al. | |
| 2017/0215723 A1 | 8/2017 | Sakurada et al. | |
| 2018/0360295 A1 | 12/2018 | Boucher et al. | |
| 2019/0059728 A1 | 2/2019 | Gilad-Gilor | |
| 2020/0260992 A1 | 8/2020 | Mirza | |

FOREIGN PATENT DOCUMENTS

| | | |
|---|---|---|
| JP | 2001-286442 | 10/2001 |
| JP | 2002-10978 | 1/2002 |
| JP | 2002-78679 | 3/2002 |
| JP | 2002-78681 | 3/2002 |
| JP | 2002-191559 A | 7/2002 |
| JP | 2003-122834 A | 4/2003 |
| JP | 2004-054489 A | 2/2004 |
| JP | 2004-166979 A | 6/2004 |
| JP | 2004-274151 A | 9/2004 |
| JP | 2005-342042 | 12/2005 |
| JP | 2014-509010 A | 4/2014 |
| JP | 2015-33472 A | 2/2015 |
| JP | 2015-35031 A | 2/2015 |
| JP | 2015-077208 A | 4/2015 |
| JP | 2015-530886 A | 10/2015 |
| JP | 2017-136131 A | 8/2020 |
| WO | WO 03/041572 A1 | 5/2003 |
| WO | 2014/160042 A2 | 10/2014 |
| WO | 2014/195623 A1 | 12/2014 |

OTHER PUBLICATIONS

Japanese Office Action dated Oct. 20, 2020, issued in corresponding Japanese Patent Application No. 2019-214314.

Japanese Office Action dated Oct. 20, 2020, issued in corresponding Japanese Patent Application No. 2019-214316.

* cited by examiner

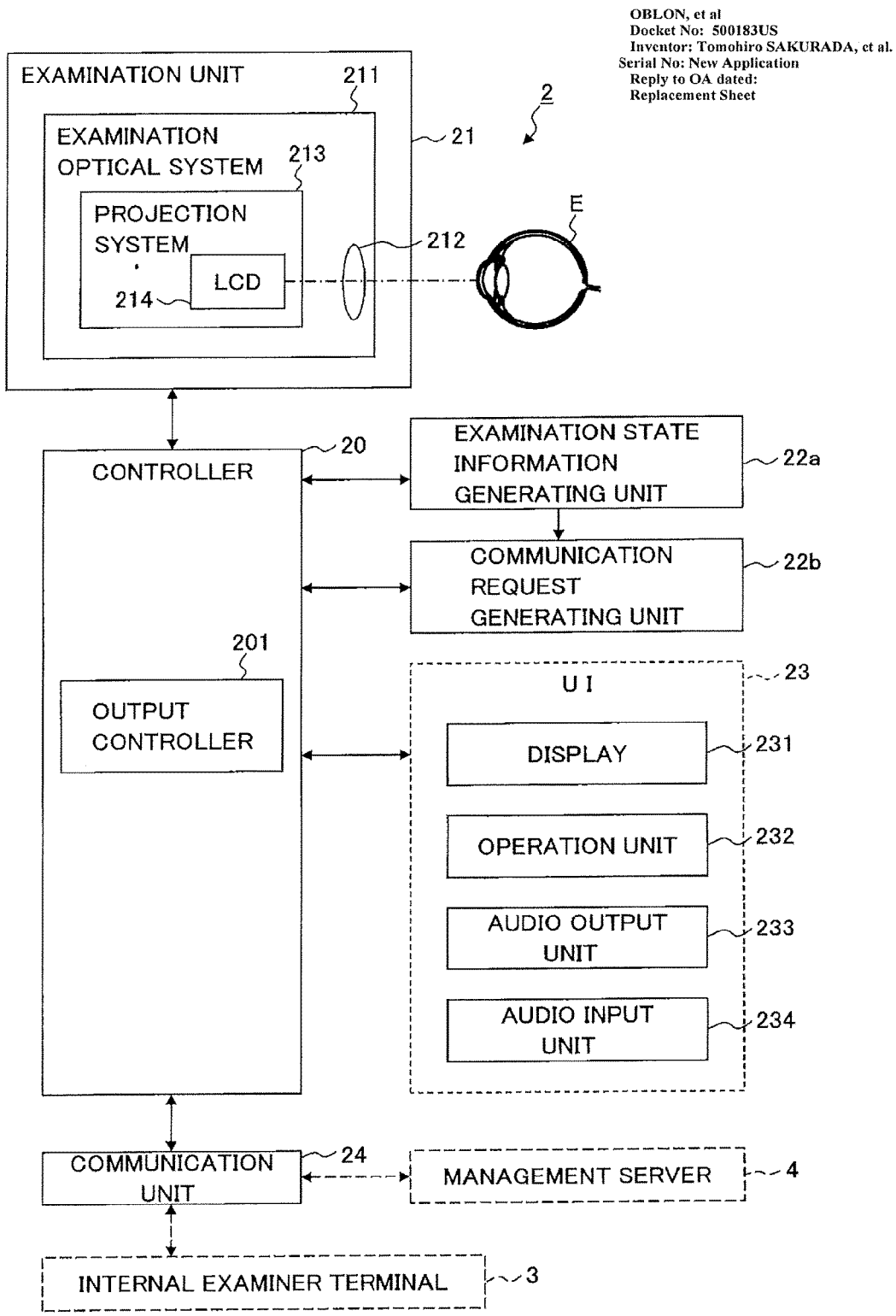

OPHTHALMIC EXAMINATION SYSTEM AND OPHTHALMIC EXAMINATION MANAGEMENT SERVER

CROSS-REFERENCE TO RELATED APPLICATION

This application is based upon and claims the benefit of priority from Japanese Patent Application No. 2016-017381, filed Feb. 1, 2016; the entire contents of which are incorporated herein by reference.

FIELD

Embodiments described herein relate generally to an ophthalmic examination system and an ophthalmic examination management server.

BACKGROUND

An ophthalmic examination apparatus is used for the examination (measurement of properties, imaging, etc.) of an eye in medical institutions, optician's stores, health check and screening venues, patient's home, and the like. Typical examples of the ophthalmic examination apparatus include the followings.
  Visual acuity test apparatus for measuring visual acuity based on a response to a visual target presented
  Eye refraction test apparatus (refractometer, keratometer) for measuring the refractive properties of the eye
  Tonometer for measuring the intraocular pressure
  Specular microscope for obtaining the properties of the cornea (corneal thickness, cell distribution, etc.)
  Wavefront analyzer for obtaining the aberration information of the eye by the use of a Hartmann-Shack sensor
  Perimeter and micro-perimeter for the detection of visual field defects
  Optical coherence tomography (OCT) for obtaining cross-sectional images, three-dimensional data, analysis data, and the like of the fundus, the anterior segment, and the like of the eye using the optical interference
  Fundus camera for photographing the fundus
  Scanning laser ophthalmoscope (SLO) for capturing images of the fundus by laser scanning using a confocal optical system
  Multifunctional apparatus having a combination of two or more functions It is often the case that the examiner instructs the subject and operates the ophthalmic examination apparatus during eye examination. In recent years, remote examination has been becoming popular. In the remote examination, the examiner, who is not present at the place where the ophthalmic examination apparatus is installed, conducts the examination while providing instructions for the subject and the ophthalmic examination apparatus (for example, see Patent Documents 1-6 listed below). The instructions for the subject include visual instructions and auditory instructions.
  Patent Document 1: Japanese Unexamined Patent Application Publication No. 2001-286442
  Patent Document 2: Japanese Unexamined Patent Application Publication No. 2002-10978
  Patent Document 3: Japanese Unexamined Patent Application Publication No. 2002-78679
  Patent Document 4: Japanese Unexamined Patent Application Publication No. 2002-78681
  Patent Document 5: Japanese Unexamined Patent Application Publication No. 2005-342042
  Patent Document 6: International Publication No. WO2003/041572

In order to efficiently implement remote examination, it is necessary to construct a system assuming various situations. For example, it is desirable to issue an appropriate instruction at an appropriate timing according to the degree of understanding of the subject with respect to contents of the examination. In the case where an examiner accompanies the subject as in the conventional case, the examiner can assist the subject by being there to perceive the state of the subject and the progress state of the examination on the spot. However, it is very difficult to put such assistance into practice with conventional technology of the remote examination. In addition, the examiner's amount of expertise and level of skill largely influence the examination to perform accurately and smoothly, but it is very difficult to assign such high-skilled examiners full-time and to every examination facility.

SUMMARY

Embodiments are intended to realize remote examination which can cope with various situations.

According to one embodiment, an ophthalmic examination system includes an ophthalmic examination apparatus, an internal examiner terminal, an external examiner terminal, and a management apparatus. The internal examiner terminal is used by an internal examiner in a facility where the ophthalmic examination apparatus is installed. The external examiner terminal is used by an external examiner outside the facility. The management apparatus is capable of communicating with each of the ophthalmic examination apparatus, the internal examiner terminal, and the external examiner terminal via a communication line. The management apparatus includes a communication establishment unit, and an information transfer unit. The communication establishment unit is capable of establishing communication between at least two apparatuses selected from the ophthalmic examination apparatus, the internal examiner terminal, and the external examiner terminal. The information transfer unit is configured to transfer information sent from one of the at least two apparatuses whose communication has been established by the communication establishment unit. Each of the ophthalmic examination apparatus, the internal examiner terminal, and the external examiner terminal includes an output unit configured to output information transferred by the information transfer unit.

According to one embodiment, it is possible to realize the remote examination that is possible to cope with various situations.

BRIEF DESCRIPTION OF THE DRAWINGS

FIG. 2 is a schematic diagram illustrating an example of the configuration of the ophthalmic examination system of the embodiment;

DETAILED DESCRIPTION

Figure 1A:
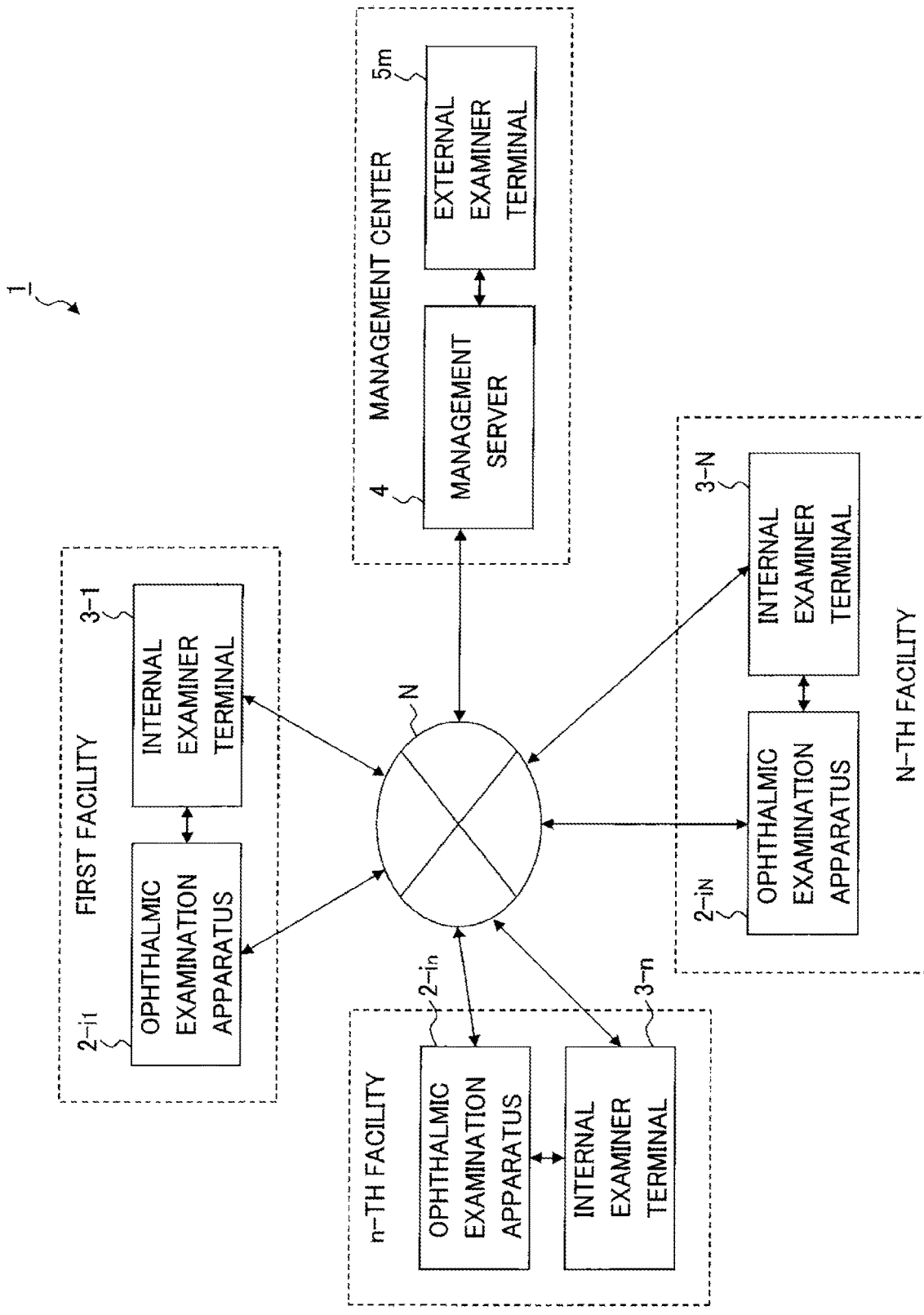
FIG. 1A is a schematic diagram illustrating an example of the configuration of an ophthalmic examination system according to an embodiment.

Referring now to the drawings, exemplary embodiments of the present invention are described below. All publications referred to herein and any known technologies are hereby incorporated by reference in their entireties.

According to one embodiment, an ophthalmic examination system is applied to remote examination in which ophthalmic examination apparatuses installed in various facilities and/or portable ophthalmic examination apparatuses are used. In the remote examination according to the embodiment, internal examiners and external examiners are involved. An internal examiner is an examiner who assists examination at a facility where an ophthalmic examination apparatus is installed. An external examiner is an examiner who assists examination from the outside of facilities where ophthalmic examination apparatus is installed. Typically, the internal examiner uses a tablet terminal or a wearable device (for example, a wireless earphone) to perceive the states of all or some subjects undergoing examination in the facility and to send instructions to each subject. The external examiner typically uses an information processing apparatus installed in a facility (management center) for managing examinations with ophthalmic examination apparatuses to perceive the states of all or some subjects currently undergoing examination and to send instructions to each subject. The subject can proceed with the examination based on the instructions sent from the internal examiner and/or the external examiner.

Examples of the facilities where the ophthalmic examination apparatuses are installed include medical institutions, optician's stores, health check and screening venues, patient's home, welfare facilities, public facilities, examination cars, and the like. In other words, the facilities where the ophthalmic examination apparatus are installed may include at least one of fixed facilities such as medical institutions and the like, and mobile facilities such as examination cars and the like. Further, the instructions sent from the examiner to the subject may include assistance (support) to the subject about how to proceed with the examination, how to use the ophthalmic examination apparatus, advices to the subject, and the like.

Note that, the aspects of the remote examination are not limited to those described above. For example, the instructions may be sent from an examiner terminal installed in a place other than the management center (e.g., the examiner's home) to the ophthalmic examination apparatus via the management center.

The ophthalmic examination apparatus may be any apparatus used for examination of a subject's eye, and may have the function of at least one of an ophthalmic measurement apparatus and an ophthalmologic imaging apparatus. The ophthalmic measurement apparatus is an apparatus for measuring the properties of the subject's eye. Example of the ophthalmic measurement apparatus include a visual acuity test apparatus (visual target presenting apparatus, phoropter, etc.), an eye refraction test apparatus (refractometer, keratometer, etc.), a tonometer, a specular microscope, a wave front analyzer, a perimeter, a micro perimeter, and the like. The ophthalmologic imaging apparatus is an apparatus for acquiring images of the subject's eye. Examples of the ophthalmologic imaging apparatus include an OCT apparatus, a fundus camera, an SLO, and the like. The ophthalmic examination apparatus may be provided with application software for analyzing measurement data and/or acquired images.

<Configuration of the Ophthalmic Examination System>

Described below is an example of the configuration of the ophthalmic examination system according to an embodiment. An ophthalmic examination system 1 illustrated in FIG. 1A as an example is configured by the use of a network (communication line N) that connects the management center with each of N facilities (first to N-th facilities) in which examination is performed.

Each of the facilities (n-th facility: n=1 to N, N is an integer equal to or larger than 1) is provided with ophthalmic examination apparatus(es) $2\text{-}i_n$ ($i_n$=1 to $K_n$, $K_n$, is an integer equal to or larger than 1). This means that, in each facility (n-th facility), one or more ophthalmic examination apparatus(es) $2\text{-}i_n$ is/are installed. The ophthalmic examination apparatus $2\text{-}i_n$ constitutes a part of the ophthalmic examination system 1. Incidentally, the ophthalmic examination system 1 may include an examination apparatus capable of examination other than ophthalmic examination.

The ophthalmic examination apparatus $2\text{-}i_n$ of this example has the function of an "examination apparatus" that performs the examination of the subject (subject's eye), and the function of a "computer" that performs various kinds of data processing and communicates with external devices. For another example, the examination apparatus and the computer may be provided separately. In this case, the examination apparatus and the computer may be configured to be capable of communicating with each other. Further, there may be arbitrary number of examination apparatuses and arbitrary number of computers. For example, there may be a single computer and a plurality of examination apparatuses.

Each facility (n-th facility) is further provided with an information processing apparatus (internal examiner terminal 3-n) used by an internal examiner. The internal examiner terminal 3-n is a computer for the use in the facility. The internal examiner terminal 3-n may be a mobile terminal such as a tablet computer or a smartphone, a server installed in the facility (in-house server, etc.), or the like. Further, the internal examiner terminal 3-n may include wearable devices such as a wireless earphone. The internal examiner terminal 3-$n$ is only required to be a computer having a function which can be used in the facility. The internal examiner terminal 3-$n$ may be, for example, a computer installed in a place other than the facility (e.g., cloud server, etc.).

The ophthalmic examination apparatus 2-$i_n$ and the internal examiner terminal 3-$n$ may be configured to be capable of communicating with each other through a network built in the n-th facility (in-house LAN, etc.), a wide area network (the Internet, etc.), near-field communication technology, or the like.

The ophthalmic examination apparatus 2-$i_n$ may include a function as a server. In the case where such a configuration is applied, the ophthalmic examination apparatus 2-$i_n$ and the internal examiner terminal 3-$n$ may be configured to communicate directly with each other. In this case, there is no need to provide a function to perform communication between the internal examiner terminal 3-$n$ and a management server 4. In other words, a configuration can be employed in which communication between the management server 4 and the internal examiner terminal 3-$n$ is performed via the ophthalmic examination apparatus 2-$i_n$.

A management server 4 is installed in the management center. The management server 4 can communicate with an external examiner terminal(s) 5$m$ (m=1 to M, M is an integer equal to or larger than 1) used by an external examiner via a network (LAN, wide area network, etc.). Further, the management server 4 can communicate with at least part of the ophthalmic examination apparatuses 2-$i_n$ installed in the first to N-th facilities via a wide area network.

The management server 4 has, for example, the function of relaying communication between the ophthalmic examination apparatus 2-$i_n$ and the external examiner terminal 5$m$, and the function of recording the contents of the communication. In addition, the management server 4 is provided with the function of associating the ophthalmic examination apparatus 2-$i_n$ with the external examiner terminal 5$m$, i.e., the function of assigning an examiner to each of the ophthalmic examination apparatuses 2-$i_n$. The correspondence between the ophthalmic examination apparatuses 2-$i_n$ and the external examiner terminals 5$m$ may be any of the one-to-one correspondence, multiple-to-one correspondence, and one-to-multiple correspondence. The management server 4 may be configured to detect the occurrence of a predetermined error in the contents of the communication between the ophthalmic examination apparatus 2-$i_n$ and the external examiner terminal 5$m$, to record the occurrence of the error, and to notify the external examiner terminal 5$m$ etc. of a warning.

Figure 1B:
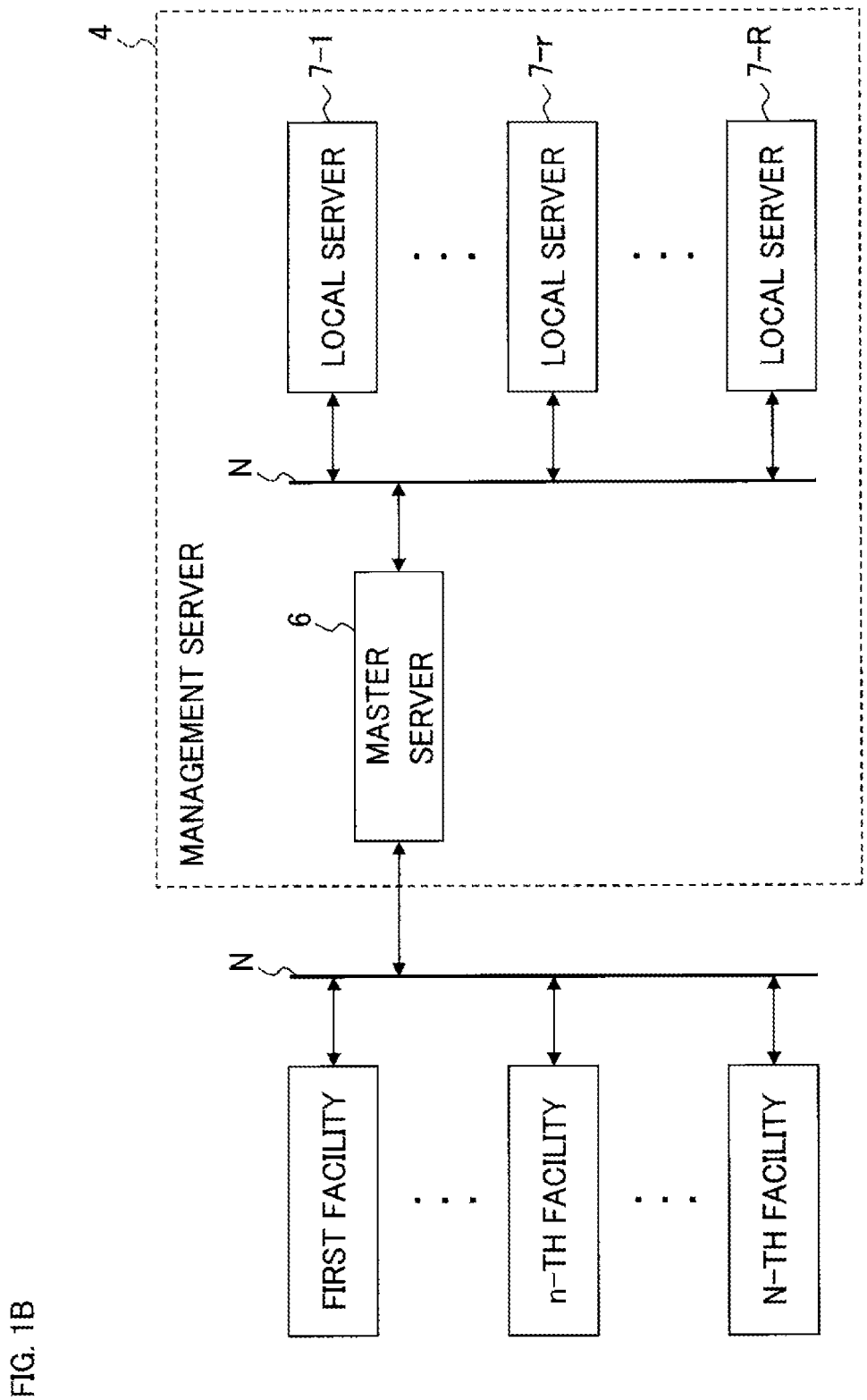
FIG. 1B is a schematic diagram illustrating an example of the configuration of the ophthalmic examination system according to an embodiment.

The management server 4 includes one or more computers. FIG. 1B illustrates an example of a case in which the management server 4 includes a plurality of computers. The management server illustrated in FIG. 1B includes a master server 6 and R local servers 7-$r$ (R is an integer equal to or larger than 2). The master server 6 and each local server 7-$r$ can communicate with each other via the communication line N. The master server 6 can communicate with the apparatuses (Here, the ophthalmic examination apparatus 2-$i_n$ is included. The internal examiner terminal 3-$n$ may be further included) installed in each of the first to Nth facilities via the communication line N. The master server 6 may be installed in a place other than the management center. Further, the master server 6 may include two or more information processing apparatuses.

In this example, two or more management centers may be provided. The local server 7-$r$ is installed, for example, in one of the management centers and manages the external examiner terminal 5$m$ in this management center. The master server 6 manages two or more local servers 7-$r$.

The configuration of the management server 4 is described later. When the management server 4 includes a plurality of computers, the components of the management server 4 (described later) are dispersedly arranged in the plurality of computers. In addition, any of the components can be provided in two or more computers in a duplicated manner. With this, for example, distributed processing and redundancy are implemented.

The external examiner terminal 5$m$ includes a computer used by an examiner who supervises and manages the examination being performed using the ophthalmic examination apparatus 2-$i_n$.

<Configuration of the Ophthalmic Examination Apparatus>

A description is given of an example of the configuration of the ophthalmic examination apparatus 2-$i_n$. The ophthalmic examination apparatus 2 illustrated in FIG. 2 as an example corresponds to each of the ophthalmic examination apparatuses 2-$i_n$ illustrated in FIG. 1A. Similarly, each of the internal examiner terminals 3-$n$ may sometimes be referred to as "internal examiner terminal 3", and each of the external examiner terminals 5$m$ may sometimes be referred to as "external examiner terminal 5".

The ophthalmic examination apparatus 2 includes a controller 20, an examination unit 21, an examination state information generating unit 22$a$, a communication request generating unit 22$b$, a user interface (UI) 23, and a communication unit 24. These constituent elements may be integrally provided (i.e., may be provided in a single housing), or may be distributed in two or more housings. Examples of the former include a refractometer, a keratometer, a tonometer, a specular microscope, a wave front analyzer, a perimeter, a micro perimeter, an OCT, a fundus camera, an SLO, and the like. Examples of the latter include a visual acuity test apparatus that includes a visual target presenting apparatus and a phoropter. Besides, part or whole of the controller 20 may be implemented by a personal computer, a portable terminal, or the like. Further, part or whole of the user interface 23 may be implemented by a personal computer, a portable terminal, a television receiver, a smart TV, or the like.

<Controller 20>

The controller 20 performs various kinds of control and operations. The controller 20 includes a processor. The "processor" as used herein is a circuit such as a central processing unit (CPU), a graphics processing unit (GPU), an application specific integrated circuit (ASIC), and a programmable logic device (PLD). Examples of PLD include a simple programmable logic device (SPLD), a complex programmable logic device (CPLD), and a field programmable gate array (FPGA), and the like. For example, the controller 20 reads a program stored in a memory circuit or a storage device, and executes the program to implement the functions of the embodiment. The controller 20 may further include RAM, ROM, a hard disk drive, a solid state drive, and the like.

<Output Controller 201>

The controller 20 includes an output controller 201. The output controller 201 performs control for outputting the information sent to the ophthalmic examination apparatus 2 from the internal examiner terminal 3 or the external examiner terminal 5. Examples of the output information include visual information and audio information. The visual information is information recognized by the sensory system for vision, and examples thereof include text information, image information, and the like. The text information includes, for example, a text message that represents an instruction from the examiner. The image information includes, for example, a moving image of the face, hand, etc. of the subject's, a mark that represents an instruction from the examiner, or the like. The output controller 201 controls a liquid-crystal display (LCD) 214 or a display 231 (described later) to output the visual information. The audio information is information recognized by the sensory system for hearing, and examples thereof include warning sound, a voice message, and the like. The output controller 201 controls an audio output unit 233 (described later) to output the audio information. Specific examples of the processes performed by the output controller 201 are described later.

<Examination Unit 21>

The examination unit 21 performs the examination of the eye under control of the controller 20. The examination unit 21 has a configuration corresponding to the kind of the ophthalmic examination apparatus 2. The configuration of the examination unit 21 may be at least part of a known configuration, or may include a known configuration. The examination unit 21 includes optical systems as described below, and mechanisms (not illustrated) such as an actuator, a power transmission mechanism.

When the examination unit 21 has the function of measuring the properties of the subject's eye E, the examination unit 21 in one example includes at least an optical system for projecting light onto the subject's eye, and may further includes an optical system for detecting return light of the light projected onto the eye. In addition, the examination unit 21 may include optical systems for various kinds of functions such as an optical system for projecting a fixation target onto the eye, an optical system for alignment, and an optical system for focusing. The examination unit 21 may also include a processor for processing the detection result of the return light (image signals, video signals, etc.).

When the examination unit 21 has the function of acquiring images of the subject's eye E, the examination unit 21 in one example includes an optical system for projecting light onto the subject's eye and an optical system for detecting return light of the light projected onto the eye. As in the case of the measurement function, the examination unit 21 may include various kinds of optical systems. The examination unit 21 may also include a processor for processing the detection result of the return light (image signals, video signals, etc.).

The optical systems as described above correspond to an examination optical system 211. The examination optical system 211 includes an optical element 212 and a projection system 213. The optical element 212 is applied to the subject's eye E to guide a light beam output from the projection system 213 to the subject's eye E. The optical element 212 may include any of various kinds of optical elements. For example, the optical element 212 may include a lens (objective lens, etc.), a prism (objective prism, etc.), a concave mirror (parabolic mirror, etc.), a glass plate, or the like.

The projection system 213 projects a light beam for examining the subject' s eye E (examination light beam) onto the subject's eye E through the optical element 212. The projection system 213 is provided with the LCD 214. The LCD 214 operates under the control of the controller 20. The LCD 214 has the function of displaying information used for examination (examination information: visual target, fixation target, etc.), and the function of displaying information received from the internal examiner terminal 3 or the external examiner terminal 5. The latter is a function of an information presenting optical system. The LCD 214 corresponds to a display of the information presenting optical system. The projection system 213 also implements the function of a light guide system that guides a light beam (display light beam), which corresponds to the information sent from the internal examiner terminal 3 or the external examiner terminal 5, from the LCD 214 to the subject's eye E through the optical element 212. That is, in the examination unit 21 of this embodiment, the configuration of the examination optical system and that of the information presenting optical system are common. In contrast, the examination optical system and the information presenting optical system may be configured separately, an example of which is described later.

<Examination State Information Generating Unit 22a>

The examination state information generating unit 22a generates examination state information indicating the state of the examination of the subject' s eye E. The examination state information includes the progress state of examination (phase or stage of examination), on-going state (interim report) of examination (e.g., the history of visual targets having been presented in a visual acuity test), examination time (e.g., examination start time, elapsed time), or the like. When the ophthalmic examination apparatus 2 has the function of acquiring images of the subject's eye E, the subject, or the like, the examination state information may include an acquired image (still image, moving image) of the subject's eye E or the like. The examination state information may include audio information of the subject input via an audio input unit 234. The examination state information generated is, for example, sent to the internal examiner terminal 3 and/or the external examiner terminal 5, and is referred to by the examiner. In this embodiment, the examination state information generated is also sent to the communication request generating unit 22b. The examination state information generating unit 22a includes, for example, a processor, and a computer program for carrying out examination or a computer program for monitoring it.

The examination state information generating unit 22a need not necessarily process all the information sent from the ophthalmic examination apparatus 2 to the internal examiner terminal 3 and/or the external examiner terminal 5. For example, the examination state information generating unit 22a may directly send the moving image of the subject's eye E, the audio information of the subject, or the like to the internal examiner terminal 3 and/or the external examiner terminal 5. With this, the state of the subject's eye E, the state of the subject, a request from the subject, or the like can be given to the examiner with substantially no time lag.

<Communication Request Generating Unit 22b>

The communication request generating unit 22b generates a request (communication request) for calling the internal examiner and/or the external examiner. The communication request generating unit 22b is configured to be capable of performing at least one of the followings: processing of generating communication request in response to an instruction from a subject; and processing of generating communication request based on the examination state information generated by the examination state information generating unit 22a.

Instructions from the subject are input by the use of the user interface 23. The instruction is input through, for example, an operation unit 232 (described later) and/or the audio input unit 234. More specifically, the subject performs a predetermined operation (pressing a button, tilting a lever, etc.) in order to call an internal examiner and/or an external examiner by the use of the operation unit 232. Further, the subject can input the request for calling by operating software keys displayed on the display 231 (described later) using the operation unit 232. Alternatively, the subject can operate software keys displayed on a touch panel display with a finger to input the request for calling. In addition, when the subject outputs a voice message indicating that he/she has not perceived the contents of the examination, a voice message indicating that he/she is in need of instructions from the internal examiner and/or the external examiner, or the like, this audio information can be detected by the audio input unit 234. According to this example, it is possible to give assistance in accordance with the subject's needs.

Described below is an example of the case for generating a communication request based on examination state information. The examination state information generating unit 22a successively generates examination state information while monitoring the examination state. The communication request generating unit 22b determines whether or not the generated examination state information corresponds to a predetermined condition. Examples of the predetermined conditions includes the followings: the examination is not proceeding (the examination is in a halt); an interim result (for example, the history of the presentation of the visual targets in the visual acuity test) is inappropriate; elapsed time from the start of the examination is long; eyelids are closed for a long time; and the fixation of the subject's eye E is inappropriate. Non-progression of the examination can be recognized, for example, by detecting that the phase (stage, step) of the examination has not shifted for a predetermined time or more (for example, by detecting that the same visual target is being presented for a predetermined time or more). Inappropriateness of the interim result of the examination can be recognized, for example, by detecting inappropriateness of the presentation order of the visual targets (for example, by detecting that the contents of subject's responses are not converging). Closed eyelids and fixation state of the eye E can be recognized by analyzing an acquired image of the eye E. Image analysis for the recognition includes, for example, detection of the pupil. According to this example, it is possible to implement automatic detection of a situation where the subject requires assistance.

The communication unit 24 sends the communication request generated by the communication request generating unit 22b to the management server 4 and/or the internal examiner terminal 3.

<User Interface 23>

The user interface 23 has the function of outputting information for the subject (and also the internal examiner), and the function of inputting information and operating instructions. For the former function, the user interface 23 includes the display 231 and the audio output unit 233. For the latter function, the user interface 23 includes the operation unit 232 and the audio input unit 234.

The display 231 includes a display device such as a flat panel display. The operation unit 232 includes operation devices such as buttons, keys, a joystick, knobs, and an operation panel provided on the cabinet or outside of the ophthalmic examination apparatus 2. The operation unit 232 may include operation devices (a mouse, a keyboard, a track pad, buttons, a touch panel, etc.) of a personal computer etc. that is connected to the ophthalmic examination apparatus 2. The user interface 23 may include a single device, such as a touch panel, that includes the display 231 and the operation unit 232, and/or a graphical user interface (GUI). The user interface 23 may include a processor and a computer program for performing operation and input based on the subject's voice input from the audio input unit 234.

The audio output unit 233 includes, for example, a circuit for processing audio information (audio signals) to be output, and a speaker for outputting the audio information processed. The audio input unit 234 includes a microphone for converting audio information into electrical signals, and a circuit for processing the electrical signals.

<Communication Unit 24>

The communication unit 24 executes data communication with the management server 4. The communication unit 24 may also be capable of executing data communication with the internal examiner terminal 3. A system of the data communication is arbitrary. For example, the communication unit 24 includes a communication interface conforming to the Internet, a communication interface conforming to LAN, a communication interface conforming to near field communication, and the like. The data communication can be either wired or wireless. The communication unit 24 may be capable of executing data communication with an external device other than the management server 4 and the internal examiner terminal 3. Data sent and received by the communication unit 24 may be encrypted. In this case, for example, the controller 20 includes an encryptor that encrypts data to be sent, and a decoder that decodes data having been received.

<Configuration of the Internal Examiner Terminal>

Figure 3:
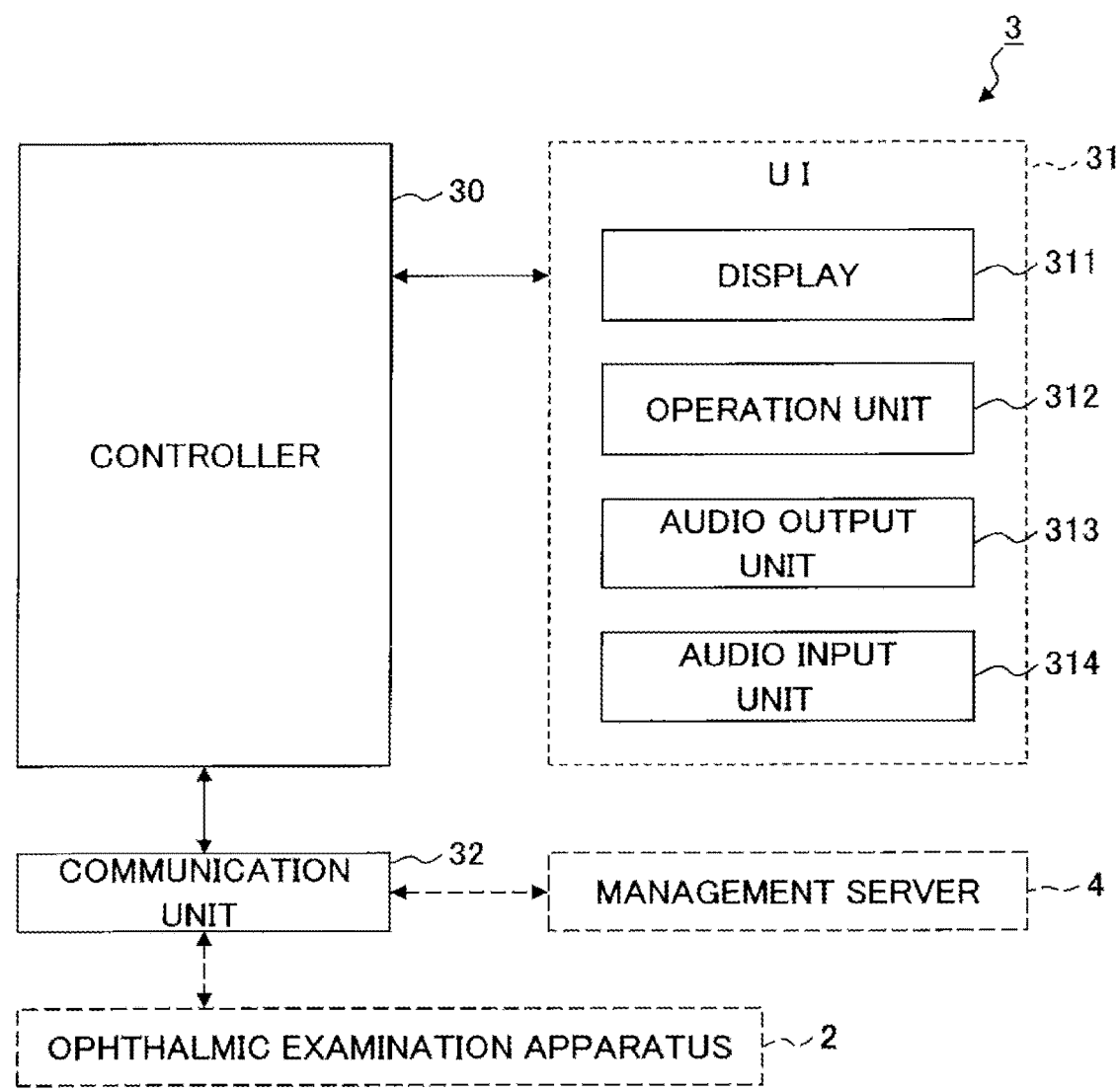
FIG. 3 is a schematic diagram illustrating an example of the configuration of the ophthalmic examination system of the embodiment.

A description is given of an example of the configuration of the internal examiner terminal 3. The internal examiner terminal 3 illustrated in FIG. 3 as an example includes a controller 30, a user interface (UI) 31, and a communication unit 32.

<Controller 30>

The controller 30 controls each unit of the internal examiner terminal 3, and performs various kinds of arithmetic operations. The controller 30 includes a processor. The controller 30 may further include RAM, ROM, a hard disk drive, a solid state drive, and the like.

<User Interface 31>

The user interface 31 has the function of outputting information for a user, and the function for allowing the user to input information and operating instructions. As with the user interface 23 of the ophthalmic examination apparatus 2, the user interface 31 includes a display 311, an operation unit 312, an audio output unit 313, and an audio input unit 314.

<Communication Unit 32>

The communication unit 32 executes data communication with the management server 4 and the ophthalmic examination apparatus 2. The system of the data communication, encryption, and the like performed by the communication unit 32 may be the same as those performed by the communication unit 24 of the ophthalmic examination apparatus 2.

<Configuration of the External Examiner Terminal>

Figure 4:
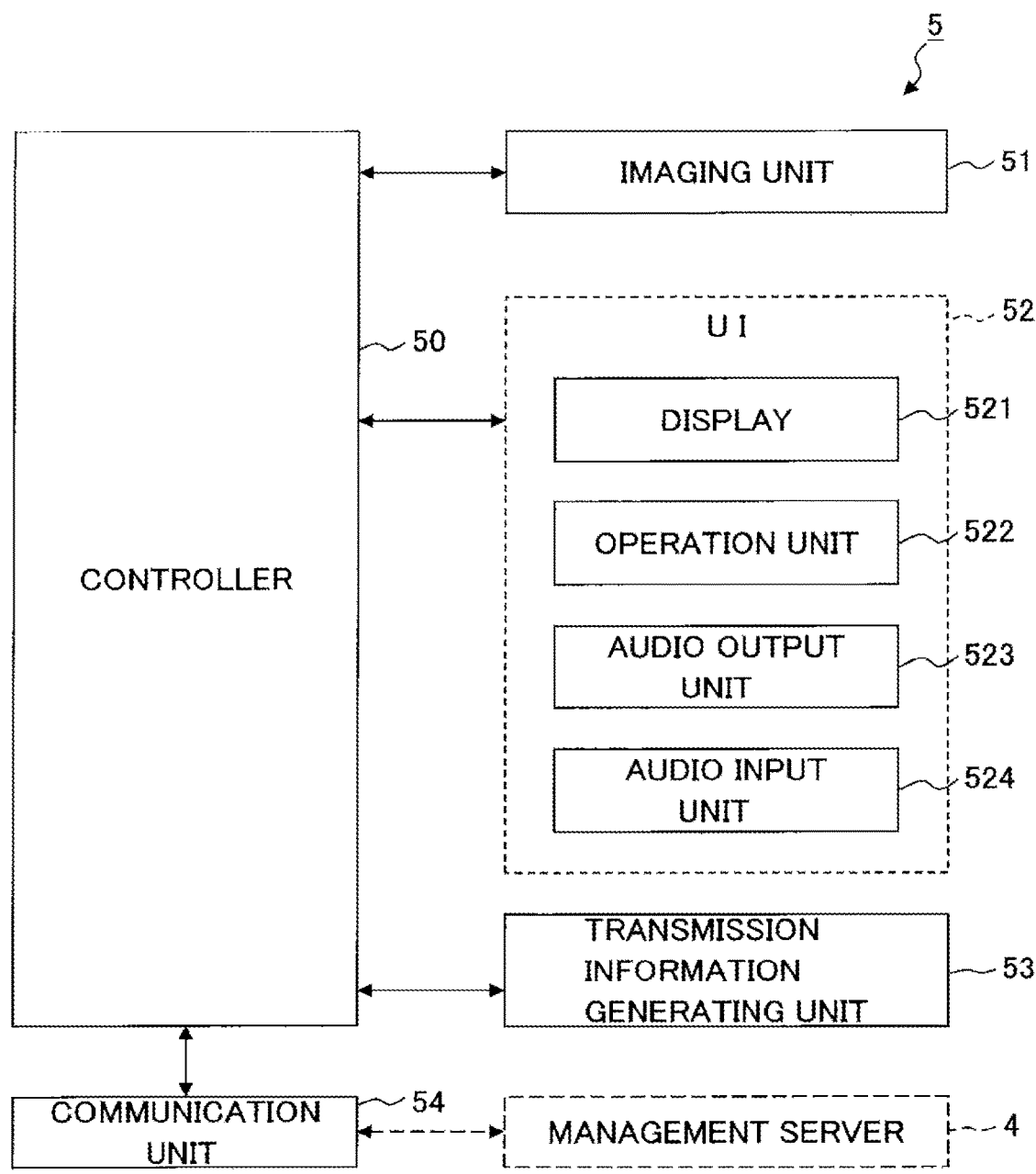
FIG. 4 is a schematic diagram illustrating an example of the configuration of the ophthalmic examination system of the embodiment.

A description is given of an example of the configuration of the external examiner terminal 5. The external examiner terminal 5 illustrated in FIG. 4 as an example includes a controller 50, an imaging unit 51, a user interface (UI) 52, a transmission information generating unit 53, and a communication unit 54.

<Controller 50>

The controller 50 controls each unit of the external examiner terminal 5, and performs various kinds of arithmetic operations. The controller 50 includes a processor. The controller 50 may further include RAM, ROM, a hard disk drive, a solid state drive, and the like.

<Imaging unit 51>

The imaging unit 51 is used to acquire a moving image of the examiner, and includes, for example, a video camera. The object to be photographed includes a body part(s) (e.g., face, upper body, hand, etc.) used to express instructions to the subject.

<User interface 52>

The user interface 52 has the function of outputting information for the examiner, and the function for allowing the examiner to input information and operating instructions. As with the user interface 23 of the ophthalmic examination apparatus 2, the user interface 52 includes a display 521, an operation unit 522, an audio output unit 523, and an audio input unit 524.

For example, the controller 50 controls the display 521 to display a screen (GUI, etc.) to present the examination state information successively received from the ophthalmic examination apparatus 2 and to enter instructions to the subject. In addition, the controller 50 controls the audio output unit 523 to output audio information of the subject. With reference to the display information and audio information, the examiner can determine the content of an instruction, and enter the instruction by the use of the operation unit 522. Meanwhile, a voice instruction is entered through the audio input unit 524.

<Transmission Information Generating Unit 53>

Based on the content (instruction) that the examiner has entered using the user interface 52, the transmission information generating unit 53 generates information (transmission information) for the subject who uses the ophthalmic examination apparatus 2. The transmission information generating unit 53 includes, for example, a processor and a transmission information generating program to be executed in conjunction with the screen (GUI).

Note that the transmission information generating unit 53 need not necessarily process all the information sent from the external examiner terminal 5 to the ophthalmic examination apparatus 2. For example, the transmission information generating unit 53 may directly send a moving image, the audio information, or the like of the examiner to the ophthalmic examination apparatus 2. With this, instructions from the examiner can be given to the subject with substantially no time lag.

<Communication Unit 54>

The communication unit 54 executes data communication with the management server 4. The system of the data communication, encryption, and the like performed by the communication unit 54 may be the same as those performed by the communication unit 24 of the ophthalmic examination apparatus 2.

<Configuration of the Management Server>

Figure 5:
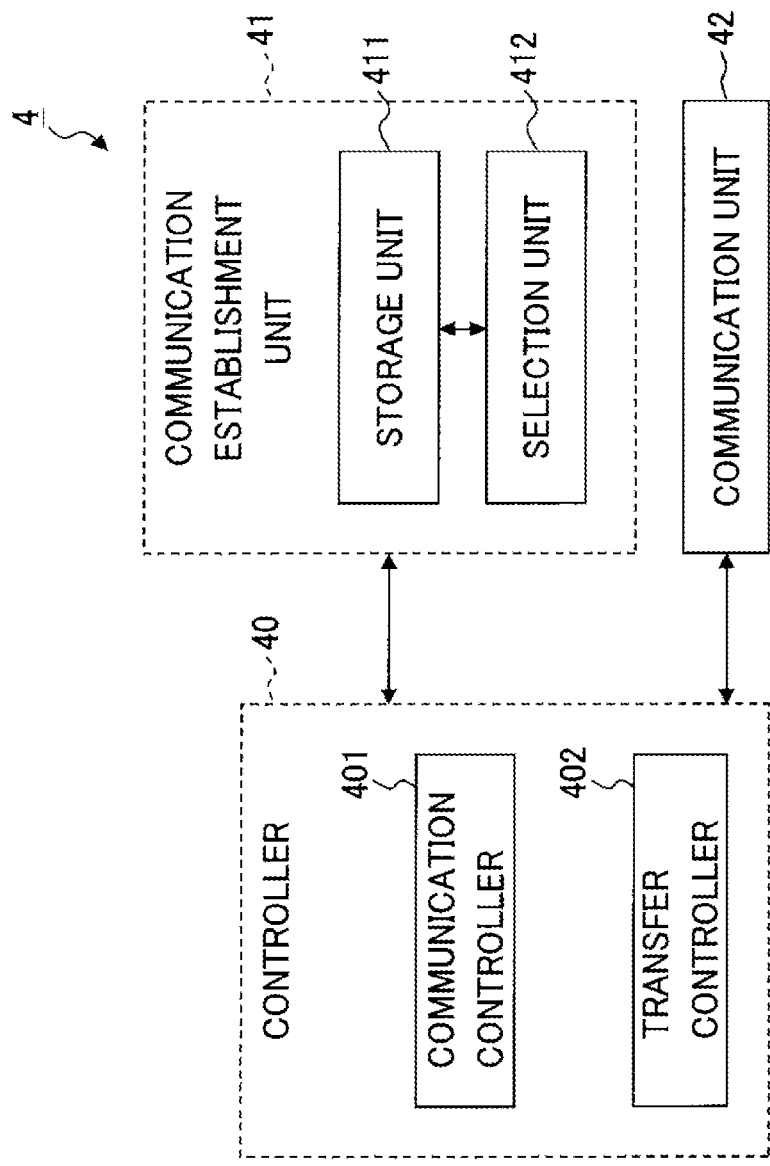
FIG. 5 is a schematic diagram illustrating an example of the configuration of the ophthalmic examination system of the embodiment.

A description is given of an example of the configuration of the management server 4. The management server 4 illustrated in FIG. 5 as an example includes a controller 40, a communication establishment unit 41, and a communication unit 42. At least one of these components is implemented, for example, by cooperation of hardware and software dispersedly arranged in the master server 6 and the local server 7-r illustrated in FIG. 1B.

<Controller 40>

The controller 40 performs control of each unit of the management server 4. For example, part of the controller 40 (master controller) may be provided in the master server 6, and the master controller may be configured to perform control of each local server 7-r. The controller 40 may be capable of executing other arithmetic operations. The controller 40 includes a processor. The controller 40 may further include RAM, ROM, a hard disk drive, a solid state drive, and the like.

The controller 40 includes a communication controller 401 and a transfer controller 402.

The communication controller 401 performs control related to the establishment of communication between the ophthalmic examination apparatus, the internal examiner terminal, and the external examiner terminal. For example, the communication controller 401 sends a control signal for establishing communication to each of the apparatuses selected from among the ophthalmic examination apparatuses, the internal examiner terminals, and the external examiner terminals by a selection unit 412 (described later).

The transfer controller 402 performs controls related to exchange of information between the apparatuses whose communication has been established by the communication establishment unit 41 (and the communication controller 401). For example, the transfer controller 402 transfers the information sent from one of at least two apparatuses whose communication has been established by the communication establishment unit 41 (and communication controller 401) to one or more of the other apparatuses. As a specific example, when communication between the ophthalmic examination apparatus 2 and the external examiner terminal 5 is established, the transfer controller 402 transfers the information sent from the ophthalmic examination apparatus 2 (or the external examiner terminal 5) to the external examiner terminal 5 (or the ophthalmic examination apparatus 2). At this time, the transfer controller 402 may transmit the information obtained by processing the information sent from the ophthalmic examination apparatus 2 (or the external examiner terminal 5) to the external examiner terminal 5 (or the ophthalmic examination apparatus 2). For example, the transfer controller 402 can extract part of the information transmitted from the ophthalmic examination apparatus 2 (or the external examiner terminal 5), and transmit the extracted information to the external examiner terminal 5 (or the ophthalmic examination apparatus 2). Further, a configuration may be employed in which the management apparatus 4 or another apparatus analyzes the information (for example, image data of the subject's eye E) transmitted from the ophthalmic examination apparatus 2 (or the external examiner terminal 5), and in which the result of the analysis (and original information) is sent to the external examiner terminal 5 (or the ophthalmic examination apparatus 2). Incidentally, the processing on the information is not limited to such extraction and analysis but may include any data processing.

<Communication Establishment Unit 41>

The communication establishment unit 41 performs processing for establishing communication between at least two apparatuses selected from the ophthalmic examination apparatuses 2, the internal examiner terminals 3, and the external examiner terminals 5. In the present embodiment, "establishment of communication" refers to a concept which includes, for example, at least one of the followings: (1) establishing unidirectional communication from a state in which communication is disconnected; (2) establishing bidirectional communication from a state in which communication is disconnected; (3) switching from a state in which only reception is possible to a state in which transmission is also possible; and (4) switching from a state in which only transmission is possible to a state in which reception is also possible. As a specific example, "establishment of communication" may include switching from a state in which the external examiner is monitoring the examination (a state in which only reception is possible) using the external examiner terminal 5 to a state in which sending instructions from the external examiner to the subject is possible.

Further, the communication establishment 41 can perform a process of disconnecting the established communication. In the present embodiment, "disconnecting communication" refers to a concept which includes, for example, at least one of the following: (1) disconnecting communication from a state in which unidirectional communication has been established; (2) disconnecting communication from a state in which bidirectional communication has been established; (3) switching from a state in which bidirectional communication has been established to unidirectional communication; (4) switching from a state in which transmission and reception are possible to a state in which only reception is possible; and (5) switching from a state in which transmission and reception are possible to a state in which only transmission is possible. As a specific example, "disconnecting communication" may include switching from a state in which the external examiner is able to send instructions to the subject (a state in which both transmission and reception are possible) using the external examiner terminal 5 to a state in which only the monitoring of the examination is possible (a state in which only reception is possible).

Each of the ophthalmic examination apparatus 2, the internal examiner terminal 3, and the external examiner terminal 5 can send at least one of the following communication requests to the management server 4: a communication request (call request) for calling another apparatus (the user thereof); and a communication request (interruption request) for interrupting communication between other two apparatuses. The call request and the interruption request are sent manually or automatically. The management server 4 (communication unit 42) receives the communication request sent from the ophthalmic examination apparatus 2, the internal examiner terminal 3, or the external examiner terminal 5.

In the embodiment, the communication establishment unit 41 may include the selection unit 412. Based on the received communication request, the selection unit 412 selects one or more apparatuses from the ophthalmic examination apparatuses 2, the internal examiner terminals 3, and the external examiner terminals 5 other than the apparatus which has sent the communication request. For example, upon receiving a communication request from the ophthalmic examination apparatus 2, the selection unit 412 selects, for example, one or both of: the internal examiner terminal 3 in the facility in which the ophthalmic examination apparatus 2 is installed; and any of the external examiner terminals 5 installed in any of the management centers (any of the local servers 7-$r$). Then, the communication establishment unit 41 establishes communication between the selected internal examiner terminal 3 and/or the selected external examiner terminal 5, and the ophthalmic examination apparatus 2 which has sent the communication request. With such processes, it is possible to automatically select an examiner(s) in accordance with a request from the subject of the ophthalmic examination apparatus 2, and to give support for the examination.

The selection of apparatuses in response to a communication request is performed, for example, based on preset attributes. Examples of the attributes include the kinds of examinations, the amounts of expertise and the levels of skill required for assisting examinations, the kinds of languages, and the like. In order to realize this example, the communication establishment unit 41 may include a storage unit 411 in which the attribute information prepared in advance is stored. The attribute information represents the attributes of the internal examiner terminals 3 and/or their users (internal examiners), and the attributes of the external examiner terminals 5 and/or their users (external examiners). Here, the internal examiners and the external examiners are identified by, for example, pre-assigned examiner identifications. Further, the internal examiner terminals 3 and the external examiner terminals 5 are identified by, for example, pre-assigned apparatus identifications or network addresses. In a typical example of the attribute information, the attributes of each examiner (each of the internal examiners and the external examiners) includes the kinds of examinations that the examiner can support, amount of expertise and the level of skill of the examiner, and the kinds of languages that the examiner can use.

When a configuration is employed in which the selection unit 412 refers to the attribution information, the communication request transmitted from the ophthalmic examination apparatus 2, the internal examiner terminal 3, or the external examiner terminal 5 may include information related to the attributes. For example, the communication request (for example, the call request) transmitted from the ophthalmic examination apparatus 2 may include any of the followings: (1) information indicating the kind of examination being performed by the ophthalmic examination apparatus 2; (2) information indicating the degree of difficulty of supporting the examination (information indicating that the subject's eye or the subject is in difficulty of undertaking the examination, information indicating the progress state of the examination, etc.); (3) information indicating the name of disease, age, or the like of the subject; and (4) information indicating the language that the subject uses. Based on the received communication request and attribute information, the selection unit 412 selects at least one from any of the internal examiner terminals 3 and any of the external terminals 5. At this time, the selection unit 412 collates the information related to the attributes included in the communication request with the information included in the attribute information. Through this process, the selection unit 412 selects, for example, the internal examiner terminal 3 and/or the external examiner terminal 5 corresponding to any of the following examiners: (1) examiners who are capable of supporting the examination of the concerned kind; (2) examiners who are capable of supporting the examination of the concerned level of difficulty; (3) examiners who are capable of supporting subjects of the concerned disease or the concerned age; and (4) examiners who are capable of using the concerned language. In such a case, the correspondence between the internal examiners and the internal examiner terminals 3, and the correspondence between the external examiners and the external examiner terminals 5 are established by, for example, using the examiner IDs input to the examiner terminals at the time of logging in. Here, apparatus IDs are assigned to the examiner terminals.

<Communication Unit 42>

The communication unit 42 performs data communication with each of the ophthalmic examination apparatus 2, the internal examiner terminals 3, and the external examiner terminals 5. The system of the data communication, encryption, and the like performed by the communication unit 42 may be the same as the communication unit 24 of the ophthalmic examination apparatus 2.

<Usage Modes>

A description is given of typical examples of usage modes of the ophthalmic examination system 1 of the present embodiment.

<First Example of Usage Mode>

Figure 6:
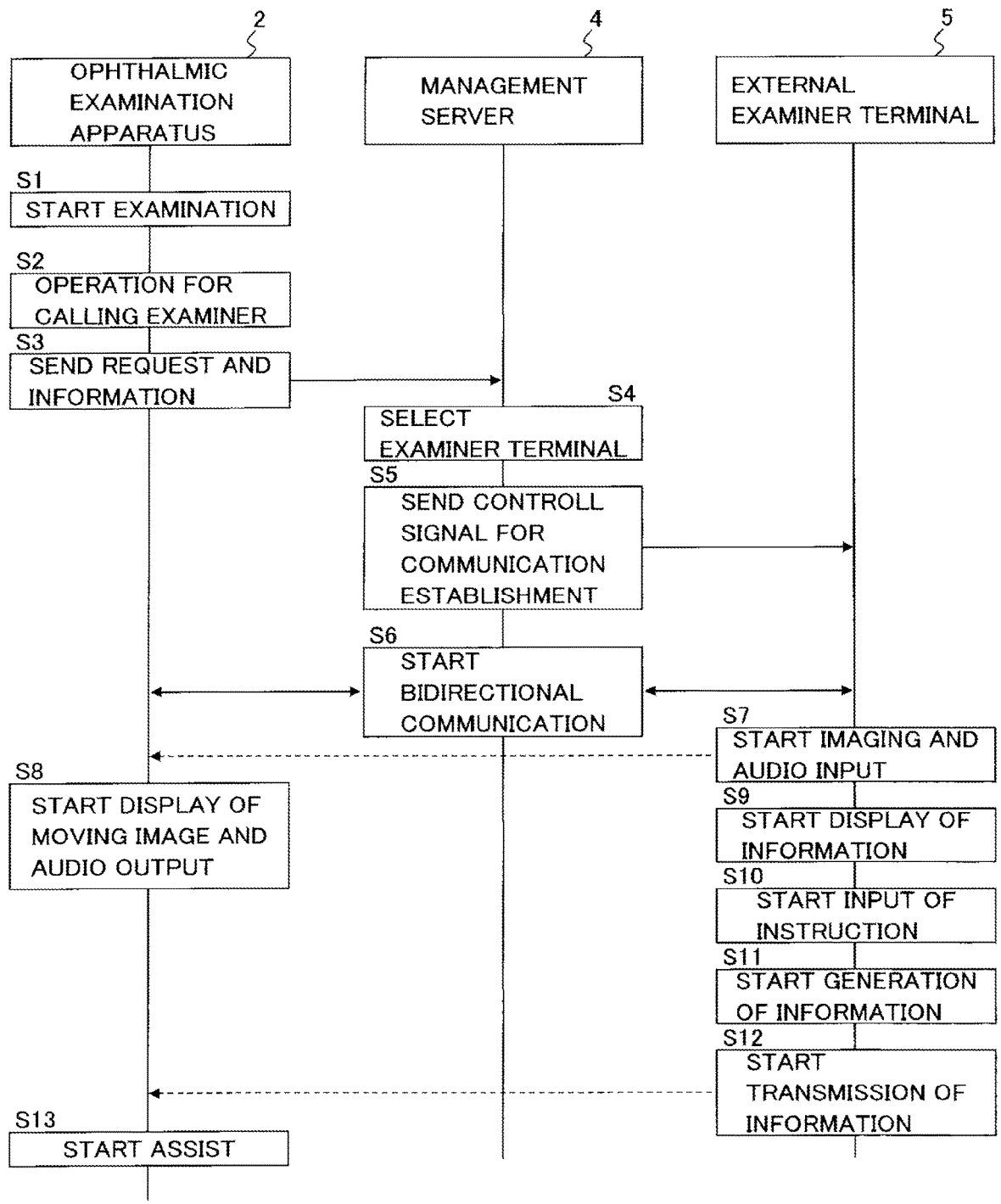
FIG. 6 is a sequence diagram illustrating an example of a usage mode of the ophthalmic examination system of the embodiment.

With reference to FIG. 6, a description is given of the first example of the usage mode of the ophthalmic examination system 1. FIG. 6 illustrates an example of the usage mode for a subject to request an examiner's assistance.

(S1: Start Examination)

Examination of the subject's eye E using the ophthalmic examination apparatus 2 starts. The communication (bidirectional communication) between the ophthalmic examination apparatus 2 and the internal examiner terminal 3 and/or between the ophthalmic examination apparatus 2 and the external examiner terminal 5 may be started in this stage. In response to the start of the examination, the controller 20 controls the examination state information generating unit 22a to start generating the examination state information.

(S2: Request for Calling Examiner)

When examiner's assistance is needed, the subject calls an examiner by the use of the user interface 23. Examples of the case where examiner's assistance is required include a case where the subject does not know how to carry out the examination, when he/she has become tired, when he/she wants to return (redo) the steps of the examination. Examples of the way how the user uses the user interface 23 in order to input the request for calling include performance of a predetermined operation with the operation unit 232, and input of voice with the audio input unit 234.

(S3: Send Request and Information)

The controller 20 controls the communication unit 24 to send the examiner call request (communication request) input in step S2 to the management server 4 together with prescribed information. Examples of the information sent with the examiner call request include identification information assigned in advance to the ophthalmic examination apparatus 2 (apparatus ID), identification information assigned in advance to the subject (subject ID), identification information assigned in advance to the facility where the ophthalmic examination apparatus 2 is installed (facility ID), at least part of the examination state information generated up to this stage, the content of the examiner call request, and the like.

(S4: Select Examiner Terminal)

The communication unit 42 of the management server 4 receives the examiner call request and the information sent from the ophthalmic examination apparatus 2 in step S3. The selection unit 412 selects an examiner to assist the subject. That is to say, the selection unit 412 selects any of the internal examiner terminals 3 located in the facility where the subject is undergoing examination, and/or any of the external examiner terminals 5.

To that end, the selection unit 412 has, for example, the function of monitoring the operating state (communication establishment information) of each of the external examiner terminals 5. In addition, the selection unit 412 can select any of the external examiner terminals 5 that is not currently running. That is, the selection unit 412 can select any of external examiners who is not currently assisting an subject). With this, it is possible to assign an external examiner who is not currently assisting other subjects to the assistance to the subject who sent the call request. Such selection processing can be implemented, for example, by managing the operating states of the respective external examiner terminals 5 by the use of the presence or absence of a flag or the like.

In another example, the selection unit 412 may be configured to determine whether or not the communication of one of the internal examiner terminal 3 and the external examiner terminal 5 corresponding to the communication request has been actually established. If the communication has not been established, the selection unit 412 can establish the communication between the ophthalmic examination apparatus 2 and the one of the internal examiner terminal 3 and the external examiner terminal 5. If the communication has already been established, the selection unit 412 can establish the communication between the ophthalmic examination apparatus 2 and the other of the internal examiner terminal 3 and the external examiner terminal 5. As a specific example, when all the internal examiner terminals 3 in the facility are currently running, that is, when all the internal examiner terminals 3 in the facility are under communication with other ophthalmic examination apparatuses 2 or with the external examiner terminals 5, the selection unit 412 can select any of the external examiner terminals 5 that is not currently running. On the other hand, when any of the internal examiner terminals 3 in the facility is not currently running, the selection unit 412 can select any of such internal examiner terminals 3. With this exemplary configuration, it is possible to give a prompt assistance to the subject by comprehensively taking into account the operating states of the internal examiner terminals 3 and the external examiner terminals 5. Incidentally, this example can also be implemented, for example, by managing the operating states of the respective internal examiner terminal 3 and the operating states of the respective external examiner terminal 5 by the use of the presence or absence of a flag or the like.

(S5: Send Control Signal for Communication Establishment)

To the examiner terminal (the internal examiner terminal 3 and/or the external examiner terminal 5) selected in step S4, the communication controller 401 sends a control signal for establishing the communication between the examiner terminal and the ophthalmic examination apparatus 2. The example illustrated in FIG. 6 represents a case in which the control signal is sent to the external examiner terminal 5.

(S6: Start Bidirectional Communication)

By the use of the control signal sent in step S5, bidirectional communication between the external examiner terminal 5 and the ophthalmic examination apparatus 2 is established. At this time, it is also possible to establish at least one of: the communication between the internal examiner terminal 3 and the external examiner terminal 5; and the communication between the internal examiner terminal 3 and the ophthalmic examination apparatus 2. As described above, such communication may be established in any of the previous stages.

(S7: Start Photographing and Audio Input)

The transfer controller 402 of the management server 4 sends the information sent from the ophthalmic examination apparatus 2 in step S3 to the external examiner terminal 5. The controller 50 of the external examiner terminal 5 controls the imaging unit 51 to start acquiring a moving image of the examiner. At this time, input of voice coming out of the examiner is also started. Image frames that the imaging unit 51 successively acquires are transferred to the ophthalmic examination apparatus 2 in a substantially real time manner via the management server 4. This transfer processing is realized mainly by the transfer controller 402.

(S8: Start Display of Moving Image and Audio Output)

The ophthalmic examination apparatus 2 receives the image frames and audio information consecutively sent from the external examiner terminal 5. The output controller 201 displays the consecutively-received image frames on the LCD 214 in a substantially real time manner. With this, the ophthalmic examination apparatus 2 can display a moving image of the examiner in a substantially real time manner. The output controller 201 also controls the audio output unit 233 to output the consecutively-received audio information in a substantially real time manner. With this, the ophthalmic examination apparatus 2 can output the voice of the examiner in a substantially real time manner.

Through the cooperative operation as above, the subject can perceive the face, gestures, voice, and the like of the examiner in a substantially real time manner. On the other hand, the examiner can also perceive the voice, operation, and the like of the subject in a substantially real time manner. Such bidirectional exchange of information can be realized mainly by the transfer controller 402 of the management server 4.

(S9: Start Display of Information)

In order to facilitate the assist work by the examiner, the controller 50 of the external examiner terminal 5 can display the screen (GUI, etc.) described above on the display 521. In addition, the controller 50 of the external examiner terminal 5 can display the information transferred from the ophthalmic examination apparatus 2 via the management server 4 (especially, the examination state information) on the screen. Upon receipt of new examination state information, the controller 50 updates the display contents. With this, the examiner can perceive the states of the examination performed using the ophthalmic examination apparatus 2 in a substantially real time manner. Further, the examiner can give appropriate assists at appropriate timings by the use of visual information and/or audio information.

(S10: Start Input of Instruction)

The examiner enters an instruction using the operation unit 522 (GUI). Examples of the contents of the instruction include change of examination, presentation of text information, presentation of image information, and the like. Besides, examples of instructions using means other than GUI include instructions by body language, instructions by voice, and the like.

(S11: Start Generation of Information)

Based on the contents (instruction) entered in step S10, the transmission information generating unit 53 generates transmission information for the subject. The transmission information is generated, for example, each time the examiner enters an instruction.

(S12: Start Transmission of Information)

The external examiner terminal 5 sends the transmission information generated in step S11 to the ophthalmic examination apparatus 2 via the management server 4. This transfer processing is realized mainly by the transfer controller 402.

(S13: Start Assist)

The ophthalmic examination apparatus 2 receives the transmission information sent from the external examiner terminal 5 in step S12. Based on the transmission information, the output controller 201 displays the moving image of the examiner and the instruction from the examiner on the LCD 214.

Described below is a specific example of the instruction for the examination. Here, it is assumed that change of examination includes the operation of switching the kinds of the visual targets used in the visual acuity test from a Landolt ring to an illustration chart. The illustration chart is a visual target made of illustrations. Specifically, for example, the illustration chart is a visual target in which familiar scenery is illustrated, and the familiar scenery includes characters and images corresponding to several levels of visual acuity scores. An instruction to change examination is performed by, for example, operating a predetermined a software key provided in the GUI. Having received the instruction to change the examination, the output controller 201 of the ophthalmic examination apparatus 2 switches the visual targets for the visual acuity test displayed on the LCD 214 from the Landolt ring to the illustration chart.

Figure 7A:
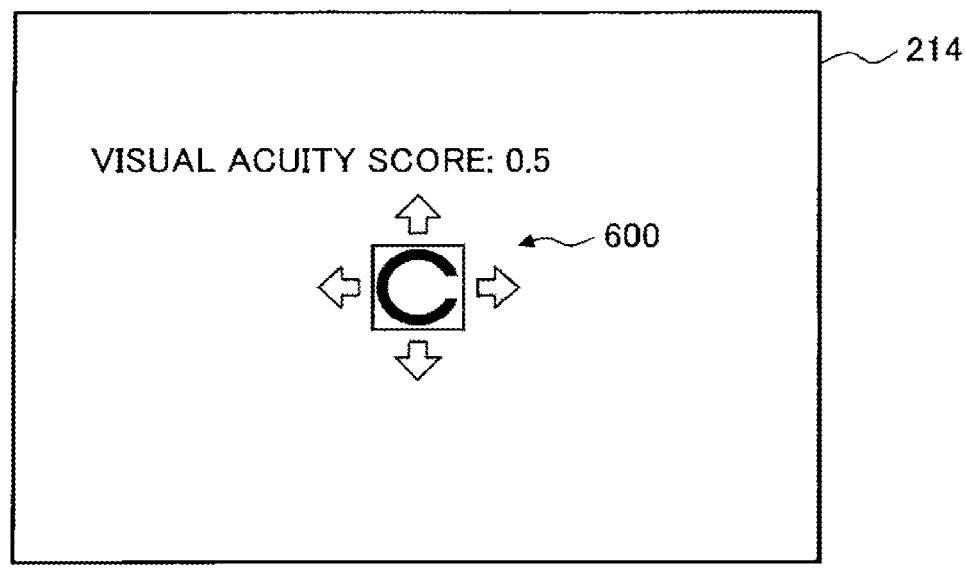
FIG. 7A is a schematic diagram for explaining a usage mode of the ophthalmic examination system of the embodiment.

FIG. 7A illustrates an example of display for visual acuity test with a Landolt ring. As illustrated in FIG. 7A, display contents 600 include a C-shaped Landolt ring. Further, the display contents 600 include a character string "visual acuity score: 0.5" representing the visual acuity score corresponding to the Landolt ring. In addition, the display contents 600 include arrow images respectively pointing up, down, left, and right directions. The arrow images are arranged around the Landolt ring. The arrow images are selectively operated to designate the direction of the gap in the Landolt ring recognized by the subject.

Figure 7B:
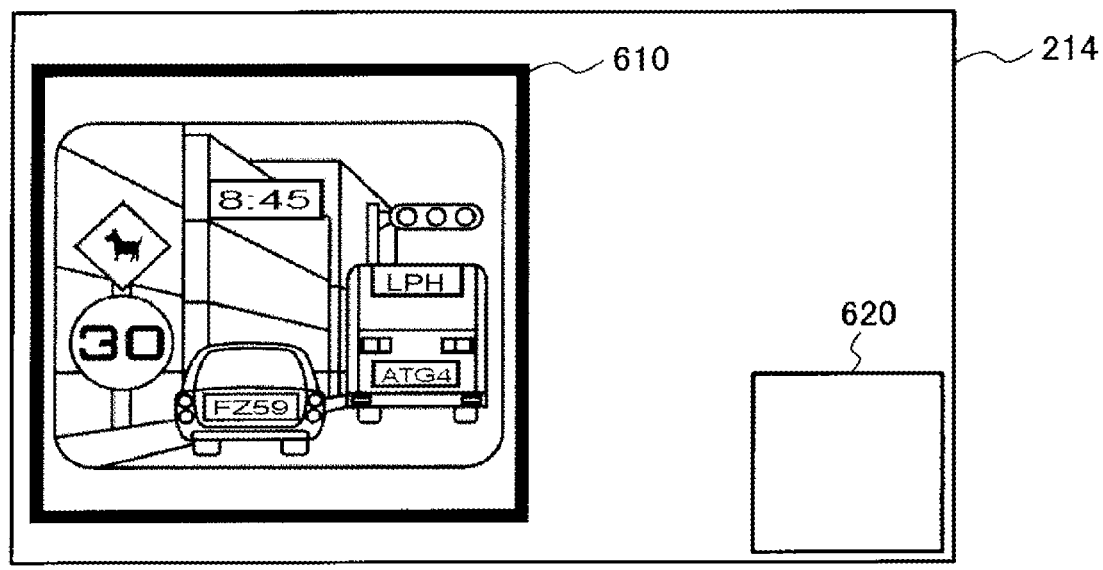
FIG. 7B is a schematic diagram for explaining a usage mode of the ophthalmic examination system of the embodiment.

FIG. 7B illustrates an example of display for visual acuity test with an illustration chart. In the example of FIG. 7B, an illustration chart 610 is displayed on the LCD 214. The illustration chart 610 illustrates an ordinary motor vehicle and a bus running on the road, road signs, a digital clock, and the like. The speed limit "30" indicated by a road sign, the time "8:45" indicated by the digital clock, the character string "LPH" indicating the destination of the bus, the character string "ATG4" written on the license plate of the bus, and the character string "FZ59" written on the license plate of the ordinary motor vehicle are in their respective sizes corresponding to different visual acuity scores. As illustrated in FIG. 7B, an examiner image display area 620 is also provided. The output controller 201 displays a moving image of the examiner being acquired by the external examiner terminal 5 in the examiner image display area 620 in a substantially real time manner.

Figure 7C:
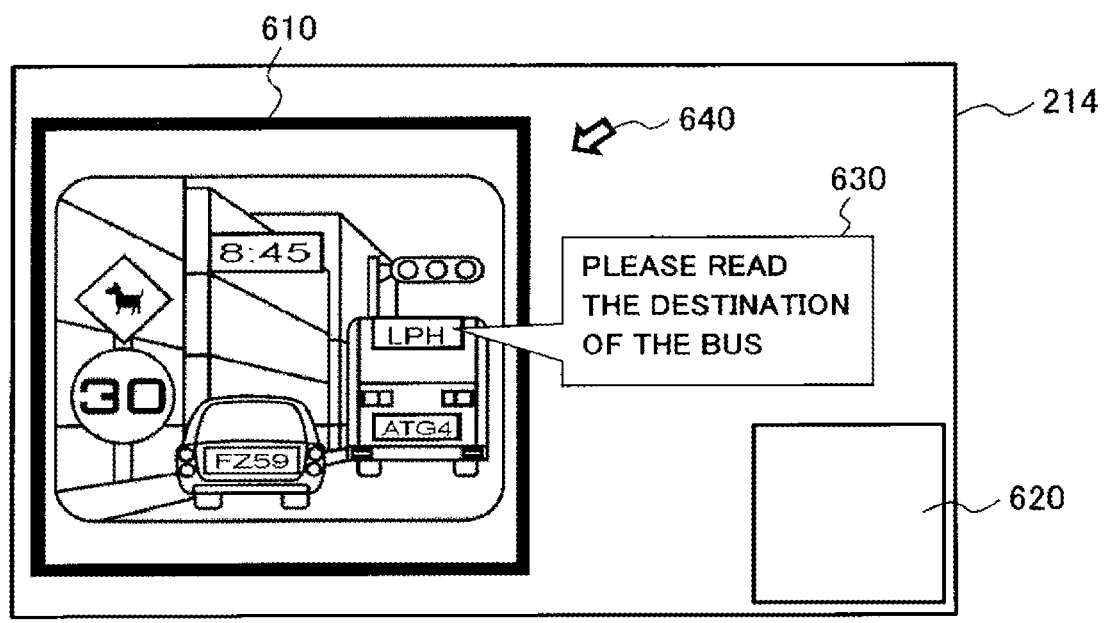
FIG. 7C is a schematic diagram for explaining a usage mode of the ophthalmic examination system of the embodiment.

FIG. 7C illustrates an example of display of an instruction from the examiner. For example, in order to make the subject read the character string "LPH" indicating the destination of the bus, the examiner performs an operation for that purpose using the GUI. Based on transmission information sent from the external examiner terminal 5, the output controller 201 displays instruction information 630 that indicates the content of instruction. The instruction information 630 of this example is a balloon image, which points to the destination of the bus, in which a character string "PLEASE READ THE DESTINATION OF THE BUS" is displayed. The examiner can give a voice instruction while displaying the instruction information 630.

The output controller 201 may be configured to adjust the display size of the instruction based on this information if the information about the sight of the subject's eye E (visual acuity score, refraction degree, etc.) has been acquired in advance. To that end, the output controller 201 may be configured to store, in advance, table information in which visual acuity scores and/or refraction degrees are associated with display sizes of character strings and/or display sizes of images. In addition, output controller 201 may be configured to select the display size associated with the visual acuity score and/or the refractive power of the subject's eye E, and configured to, when the contents of the instruction includes text information and/or image information, display the text information and/or the image information in the selected display size on the LCD 214.

In the example of FIG. 7C, a pointer 640 is also displayed. The examiner can move the pointer 640 in a substantially real time manner by the use of the GUI. With this, the examiner can inform the subject of the position of the destination display of the bus and the like.

<Second Example of Usage Mode>

Figure 8:
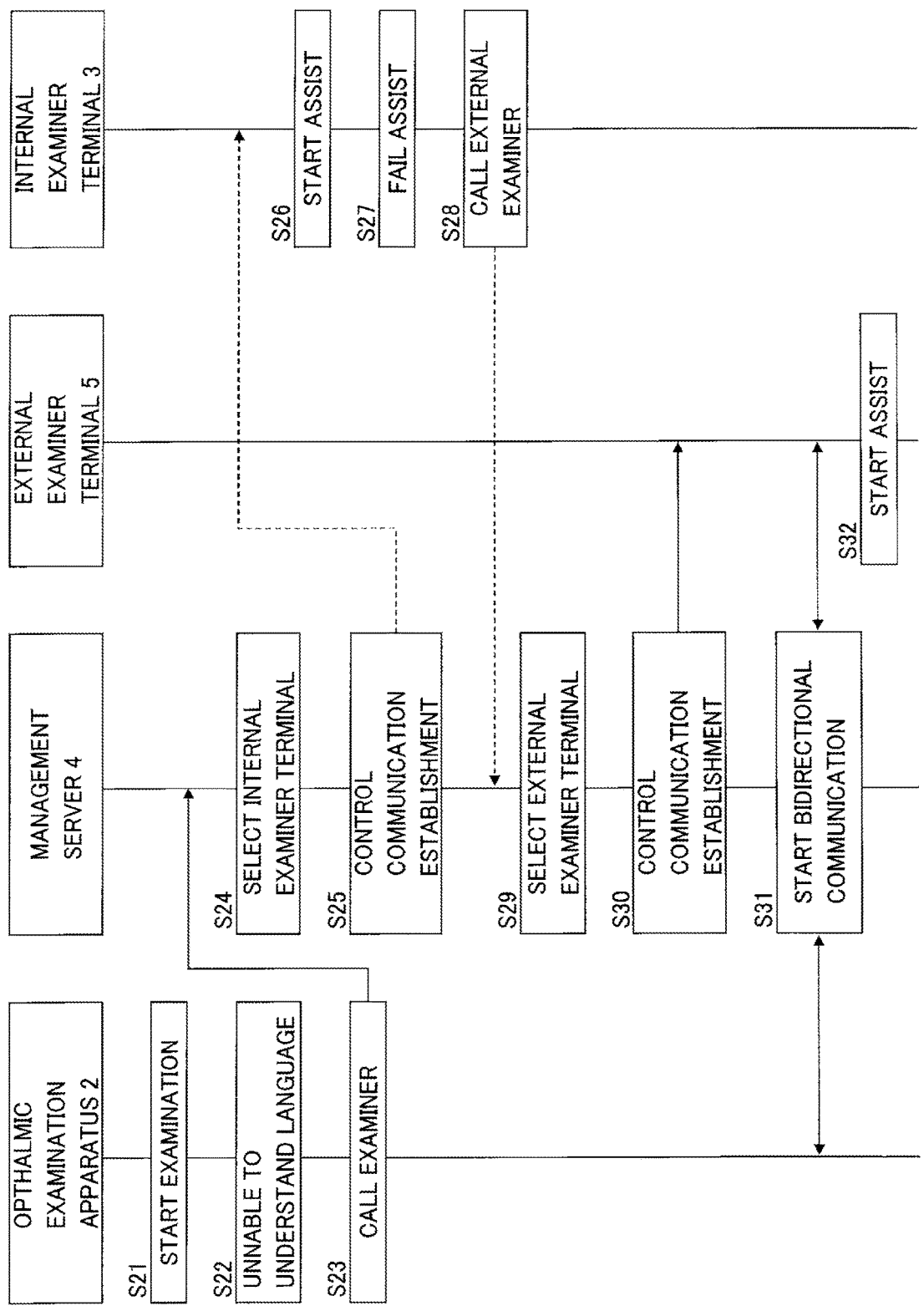
FIG. 8 is a sequence diagram illustrating an example of a usage mode of the ophthalmic examination system of the embodiment.

As a second example of the usage mode of the ophthalmic examination system 1, a usage mode for providing an assist by selecting an examiner having an attribute according to the subject will be described with reference to FIG. 8. In this example, a case will be described in which the examiner is selected according to the language used by the subject. However, the kind of the attribute that can be referred to in the selection of the examiner is not limited to the language, and may be arbitrary. For example, when the examination cannot be performed smoothly for reasons such as the subject being an elderly or the like, substantially the same processing as described below can be performed. It should be noted that descriptions of steps and processes similar to those of the first example are sometimes omitted.

(S21: Start Examination)

In this example, a subject is a person whose mother tongue is a language (for example, English) other than Japanese, and who has an insufficient understanding of Japanese. In addition, such a subject carries out an examination by the use of the ophthalmic examination apparatus 2 installed in a facility located in Japan. The examination of the subject's eye E using the ophthalmic examination apparatus 2 starts.

(S22: Unable to Understand Language)

The ophthalmic examination apparatus 2 performs giving explanations and instructions (automatic navigation) of examination directed to the subject in a language set in advance. In this example, the ophthalmic examination apparatus 2 has been set to use Japanese in the automatic navigation. As described above, the subject of this example is unable to understand the automatic navigation performed in Japanese.

(S23: Call Examiner)

When the subject performs a predetermined operation or voice input to request examiners' assistance, the communication request generating unit 22b generates a communication request (call request) based thereon. The communication unit 24 then sends the communication request and predetermined information to the management server 4. In an alternative example, the examination state information generating unit 22a of the ophthalmic examination apparatus 2 generates examination state information, and the communication request generating unit 22b generates a communication request (call request) based thereon. The communication unit 24 then sends the call request and predetermined information to the management server 4.

(S24: Select Internal Examiner Terminal)

The communication unit 42 of the management server 4 receives the examiner call request and the information transmitted from the ophthalmic examination apparatus 2 in step S23. At this stage the selecting unit 412 selects, as an examiner who assists the subject, any of the internal examiner terminals 3 existing in the facility where the subject is undergoing examination.

(S25: Control Communication Establishment)

The communication controller 401 transmits a control signal to the internal examiner terminal 3 selected in step S24 for establishing communication between the internal examiner terminal 3 and the ophthalmic examination apparatus 2.

(S26: Start Assist)

When the communication between the internal examiner terminal 3 and the ophthalmic examination apparatus 2 is established by the control in step S25, the internal examiner who uses this internal examiner terminal 3 checks the state (situation) of the subject. For example, the internal examiner can check the state by talking directly with the subject. Alternatively, the internal examiner can check the state by communicating with the subject by the use of the communication established in step S25.

(S27: Fail Assist)

If the internal examiner can cope with the state, the internal examiner continues the assistance to the subject. On the other hand, if it is determined that the state cannot be dealt with, the internal examiner proceeds to step S28 in order to ask an external examiner for assistance. Hereinafter, the latter case will be described.

(S28: Call External Examiner)

The internal examiner performs a predetermined operation using the internal examiner terminal 3 in order to ask an external examiner for assistance. This operation may include, for example, an operation of selecting a language used by the subject. In the case where the call request or the information transmitted from the ophthalmic examination apparatus 2 to the management server 4 in step S23 includes information indicating the language (English) of the subject being used, the internal examiner need not perform a language selection operation. The communication unit 32 transmits a communication request for calling an external examiner (and predetermined information) to the management server 4.

(S29: Select External Examiner Terminal)

The communication unit 42 of the management server 4 receives the communication request etc. transmitted from the internal examiner terminal 3 in step S28. At this stage, the selection unit 412 selects an external examiner who can use English (or a corresponding external examiner terminal 5) by referring to the attribute information. At this time, the selection unit 412 may select a single external examiner from among external examiners who can use English according to the operating states of such external examiners.

(S30: Control Communication Establishment)

To the external examiner terminal 5 selected in step S29 (or to the external examiner terminal 5 used by the external examiner selected in step S29), the communication controller 401 transmits a control signal for establishing communication between the external examiner terminal 5 and the ophthalmic examination apparatus 2.

(S31: Start Bidirectional Communication)

By the use of the control signal transmitted in step S30, bidirectional communication between the external examiner terminal 5 and the ophthalmic examination apparatus 2 is established. At this time, it is possible to establish communication between the internal examiner terminal 3 and the external examiner terminal 5. It is also possible to continue the establishment of communication between the internal examiner terminal 3 and the ophthalmic examination apparatus 2.

(S32: Start Assist)

When the bidirectional communication between the external examiner terminal 5 and the ophthalmic examination apparatus 2 has started in step S31, the external examiner who is the user of this external examiner terminal 5 remotely performs assistance to the subject in English.

According to the present example, it is possible to promptly start direct communication with a subject who cannot undergo examination smoothly. As a result, a sense of security can be given to the subject. Even when the problem cannot be solved by the direct communication, it is possible to automatically select an external examiner suitable for solving the problem to provide remote assistance. Therefore, it is possible to cope with various subjects without always having internal examiners of various attributes assigned to each facility.

<Modification Example of Ophthalmic Examination Apparatus>

Figure 9:
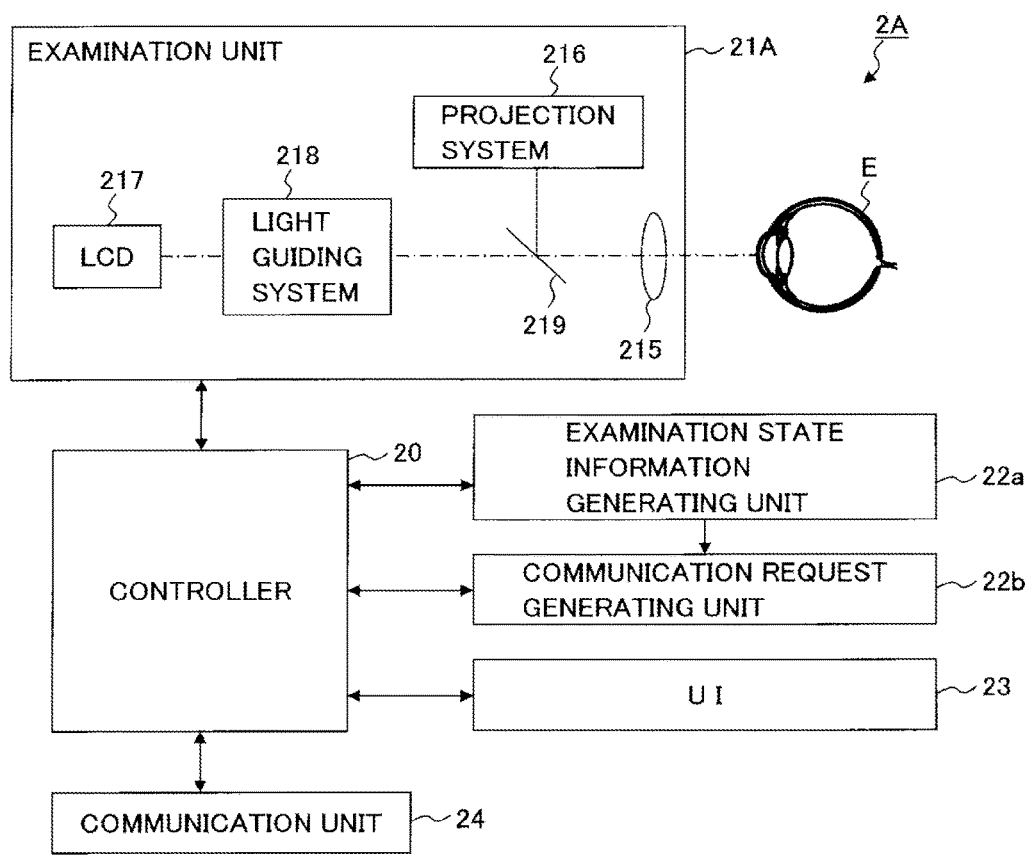
FIG. 9 is a schematic diagram illustrating an example of modification of the embodiment.

FIG. 9 illustrates an example of an ophthalmic examination apparatus in which the examination optical system and the information presenting optical system are separately arranged. In the examination unit 21A of the ophthalmic examination apparatus 2A, the examination optical system used for the examination of the subject's eye E includes an optical element 215 and a projection system 216. The optical element 215 is applied to the subject's eye E. The projection system 216 is configured to project an examination light beam for examining the eye E through the optical element 215 onto the eye E. Further, the information presenting optical system for presenting information to a subject includes an LCD 217 (display) and a light guide system 218. The light guide system 218 is configured to guide a display light beam output from the LCD 217 to the subject's eye E through the optical element 215. Examples of the information presented by the information presenting optical system includes information automatically presented by the ophthalmic examination apparatus 2A, information transmitted from the internal examiner terminal 3 (e.g., instructions from internal examiners, etc.), information transmitted from the external examiner terminal 5 (e.g., instructions from external examiners, etc.), and the like.

A beam splitter 219 combines the optical path of the examination optical system and the optical path of the information presenting optical system with each other. The beam splitter 219 may be, for example, a half mirror, a dichroic mirror, or a polarization beam splitter. Incidentally, the configuration may be basically the same as that illustrated in FIG. 2 except the examination unit 21.

Whether to configure the examination optical system and the information presenting optical system integrally as illustrated in FIG. 2 or configure them separately as illustrated in FIG. 9 is determined depending on, for example, the functions of the ophthalmic examination apparatus.

<Presentation of Information by Examiner Terminal>

Configuration and processing for presenting information to examiners will be described. As described above, the external examiner assists the subject from a remote location. Therefore, it is desirable that the system can give, to the external examiner, information for properly perceiving the states of the subject at appropriate timings by the use of an appropriate interface. It is also possible to present information to the internal examiner in the same way. In this case, the management server 4 (in particular, the transfer controller 402) may be configured to perform control so as to synthesize the presentation of information in the external examiner terminal 5 and the presentation of information in the internal examiner terminal 3.

Figure 10:
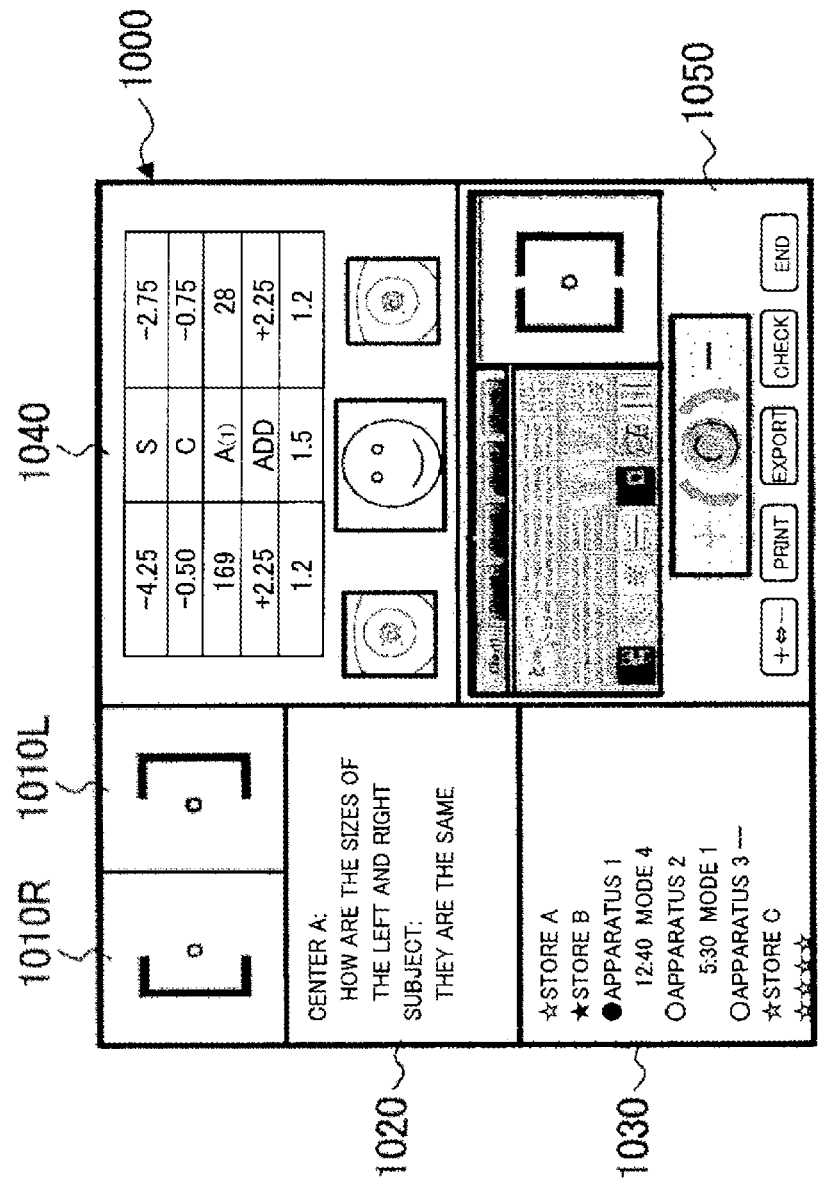
FIG. 10 is a schematic diagram illustrating an example of a display screen of the ophthalmic examination system of the embodiment

The controller 50 of the external examiner terminal 5 controls the display 521 to display the screen 1000 shown in FIG. 10. The screen 1000 is provided with presentation information display areas 1010L and 1010R, a communication content display area 1020, a use state display area 1030, a subject information display area 1040, and a presentation information operation area 1050.

In the presentation information display areas 1010L and 1010R, information currently presented to the left eye and the right eye of the subject is displayed, respectively. In the present example, the ophthalmic examination apparatus 2 is configured to be able to present information to both left and right eyes of a subject at the same time. In the ophthalmic examination apparatus 2, for example, an examination optical system and an information presenting optical system for the left eye, and an examination optical system and an information presenting optical system for the right eye are provided independently of each other (for example, an optical head for left eye and an optical head for right eye are provided). As another example, the ophthalmic examination apparatus 2 may be configured to split a light beam from a single examination optical system into two light beams, and guide one of the two light beams to the left eye and the other to the right eye, separately. As still another example, the ophthalmic examination apparatus 2 may be configured to split a light beam from a single information presenting optical system into two light beams, and guide one of the two light beams to the left eye and the other to the right eye, separately. The configuration capable of simultaneously presenting information to both left and right eyes is not limited to these, and may be of any configuration.

In the presentation information display areas 1010L and 1010R shown in FIG. 10, visual targets for binocular vision function test are displayed. These are the visual targets currently presented to the subject by the ophthalmic examination apparatus 2. Information indicating currently displayed targets is transmitted from the ophthalmic examination apparatus 2 to the management server 4, and further transferred to the external examiner terminal 5 by the transfer controller 402. Based on the information transferred from the management server 4, the controller 50 specifies the kind of the visual targets currently presented by the ophthalmic examination apparatus 2, and displays images representing the specified targets on the presentation information display areas 1010L and 1010R. The images representing the visual targets are stored in advance in a storage unit (not illustrated) in the controller 50 as a thumbnail, for example. When the visual targets presented by the ophthalmic examination apparatus 2 are changed, the aforementioned transfer process is executed in a substantially real time manner. Thereby, the external examiner can recognize the visual targets presented by the ophthalmic examination apparatus 2 in a substantially real time manner.

In the communication content display area 1020, communication contents between the examiner and the subject, in particular, contents of support provided to the subject from the examiner are displayed. The contents of the assistance displayed here may include at least one of the followings: contents of the support given by the external examiner, contents of the support given by the internal examiner, and information (contents of the questions, contents of the responses, etc.) from the subject. In addition, the ophthalmic examination system 1 may be configured to switch information on each user (external examiner, internal examiner, and subject) and to display it in the communication content display area 1020. The ophthalmic examination system 1 may also be configured to display information from one or more users in chronological order.

In the example shown in FIG. 10, the contents of the question issued by the external examiner in the management center "A" (the person using the screen 1000) and the contents of the subject's response to the question are displayed on the communication content display area 1020. It is also possible to convert the voice information issued by the examiner or the subject into text by the use of a known voice recognition technology. Further, text information that has been previously associated with a predetermined operation may be displayed.

In the use state display area 1030, the names of a plurality of facilities in which the ophthalmic examination apparatus 2 is installed, "store A", "store B", and the like are displayed.

Furthermore, identification information "apparatus 1", "apparatus 2", and the like of a plurality of ophthalmic examination apparatuses 2 installed in a facility (for example, "store B") selected from among the plurality of facilities by the external examiner or the management server 4 or the like is displayed.

In the example shown in FIG. 10, the symbol presented on the left side of the facility name indicates whether or not the facility is selected. For example, the white star symbol attached to the "store A" and the "store C" indicates that these facilities are not selected, and the black star symbol attached to the "store B" indicates that the facility is selected. Note that such star symbols may be configured as radio buttons. With such radio buttons, the external examiner can select a desired one from among these facilities.

Further, the symbol presented on the left side of the identification information of the apparatus installed in the selected "store B" likewise indicates whether or not it has been selected by the external examiner, the management server 4, or the like. In the example shown in FIG. 10, the white circle symbol indicates that it has not been selected, and the black circle symbol indicates that it is selected. In the example shown in FIG. 10, the ophthalmic examination apparatus 2 with the identification information "apparatus 1" installed in the "store B" is selected as the ophthalmic examination apparatus 2 (subject) for which the external examiner is in charge of assistance. Note that such circle symbols may be configured as radio buttons. With such radio buttons, the external examiner can select a desired one from among these ophthalmic examination apparatuses 2.

On the right side of the identification information of the ophthalmic examination apparatus 2, time information and the communication establishment state (communication mode) relating to the ophthalmic examination apparatus 2 are presented. The time information is, for example, the time when the support was started, the elapsed time from the support start, etc.

The communication modes will now be described. In the present embodiment, four communication modes can be selectively applied. Further, it is possible to shift from one communication mode to another communication mode in an arbitrarily manner.

The "communication mode 1" shows a state in which the subject is undergoing examination by him/herself with the ophthalmic examination apparatus 2. In the "communication mode 1", the subject is not receiving assistance from either the internal examiner or the external examiner. As for the ophthalmic examination apparatus 2, no communication is established with either the internal examiner terminal 3 or the external examiner terminal 5. As described above, even when the "communication mode 1" is applied, information (examination state information, information to be displayed on the screen 1000, etc.) from the ophthalmic examination apparatus 2 may be transferred to at least one of the internal examiner terminal 3 and the external examiner terminal 5. With this, the examination by the ophthalmic examination apparatus 2 can be monitored and the examiner can issue a communication request as necessary to start the support. Also, when the subject requests assistance, it is possible to respond promptly to the request.

The "communication mode 2" shows a state in which the subject is undergoing examination while receiving assistance from an external examiner. In the "communication mode 2", communication between the ophthalmic examination apparatus 2 and the external examiner terminal 5 is established. As described above, even when the "communication mode 2" is applied, information from the ophthalmic examination apparatus 2 can be transferred to the internal examiner terminal 3. With this, the internal examiner can respond promptly, for example, when it is necessary to directly assist the subject.

The "communication mode 3" shows a state in which the subject is undergoing examination while receiving assistance from an internal examiner. In the "communication mode 3", communication between the ophthalmic examination apparatus 2 and the internal examiner terminal 3 is established. As described above, even when the "communication mode 3" is applied, information from the ophthalmic examination apparatus 2 can be transferred to the external examiner terminal 5. With this, the external examiner can respond promptly, for example, when a situation which an internal examiner is unable to manage arises.

The "communication mode 4" shows a state in which a subject is undergoing examination while receiving assistance from both the internal examiner and the external examiner. In the "communication mode 4", communication between the three apparatuses (namely, the ophthalmic examination apparatus 2, the internal examiner terminal 3, and the external examiner terminal 5) is established. The "communication mode 4" is applied, for example, when it is necessary for the internal examiner and the external examiner to discuss or when the external examiner is training the internal examiner. The transfer controller 402 of the management server 4 can perform control so as not to transfer the communication contents between the internal examiner and the external examiner to the ophthalmic examination apparatus 2. That is, the transfer controller 402 can perform the following control: the transfer controller 402 transfers information from the internal examiner to the external examiner only to the external examiner terminal 5; the transfer controller 402 transfers information from the external examiner to the internal examiner only to the internal examiner terminal 3; the transfer controller 402 transfers information from the internal examiner to the subject to the external examiner terminal 5 and the ophthalmic examination apparatus 2; the transfer controller 402 transfers information from the external examiner to the subject to the internal examiner terminal 3 and the ophthalmic examination apparatus 2; and the transfer controller 402 transfers information output from the ophthalmic examination apparatus 2 to the external examiner terminal 5 and the internal examiner terminal 3.

Switching of the communication mode is performed by the management server 4 upon receiving a communication request (call request, interruption request) from the subject, the internal examiner, or the external examiner. For example, when a call request from the subject is issued in the "communication mode 1", the communication mode gets switched to 2, 3 or 4. The communication mode to be switched to is determined, for example, according to the designation by the subject, the contents of the examination state information, the aforementioned attributes, or the like.

When an interruption request from the internal examiner is issued in the "communication mode 1", the communication mode is switched to 3 or 4. Similarly, when an interruption request from the external examiner is issued in the "communication mode 1", the communication mode is switched to 2 or 4. Note that disconnection of the communication (leaving the state in which communication is established) is performed, for example, according to the selection of the examiner, the selection of the subject, the end of the examination, or the like.

In the subject information display area 1040, information on the subject is presented. In the example shown in FIG. 10, the measurement values (refractivity, astigmatism degree, astigmatic axis angle, addition degree, visual acuity value, etc.) of each eye of the subject, the anterior segment image of each eye, the face image of the subject, and the like are displayed. Furthermore, it is also possible to present arbitrary information related to the subject, such as name, age, sex, disease name, language used, level of difficulty in the examination, and the like.

In the presentation information operation area 1050, a GUI (software keys, etc.) for operating information presented to the subject is provided. In the example shown in FIG. 10, a GUI (choices of visual targets, dial for changing degrees, etc.) for selecting visual targets presented to the subject, and various operation buttons (print, export, etc.) are provided. The external examiner operates software keys or the like provided in the presentation information operation area 1050 by the use of the operation unit 522.

<Actions and Effects>

The actions and effects of the embodiment will be described.

According to the embodiment, the ophthalmic examination system includes an ophthalmic examination apparatus (2), an internal examiner terminal (3), an external examiner terminal (5), and a management apparatus (management server 4). The internal examiner terminal is used by an internal examiner in the facility where the ophthalmic examination apparatus is installed. The external examiner terminal is used by an external examiner outside the facility. The management apparatus can communicate with each of the ophthalmic examination apparatus, the internal examiner terminal, and the external examiner terminal via a communication line (N).

The management apparatus includes a communication establishment unit (41) and an information transfer unit (transfer controller 402, communication unit 42, etc.). The communication establishment unit is configured to be able to establish communication between at least two apparatuses selected from the ophthalmic examination apparatus, the internal examiner terminal, and the external examiner terminal. The information transfer unit is configured to transfer the information transmitted from one of the at least two apparatuses whose communication has been established by the communication establishment unit to another apparatus.

Each of the ophthalmic examination apparatus, the internal examiner terminal, and the external examiner terminal includes an output unit (a display, an audio output unit) that outputs the information transferred by the information transfer unit.

According to such an embodiment, it is possible to cope with various situations arising in the remote examination. For example, it is possible to promptly assist the subject according to the needs of the subject or judgment of the examiner. In addition, it is possible to issue an appropriate instruction at an appropriate timing according to the degree of understanding of the subject about the examination contents. Further, even when no examiner is accompanying the subject, it is possible to assist the subject by perceiving the state of the subject and the progress state of the examination in a substantially real time manner. It is also possible to accurately assign an examiner having a necessary ability to appropriately give assistance (an examiner with a high degree of expertise, an expert, an examiner who can use a foreign language, etc.) to the subject.

In the embodiment, the management apparatus may include a communication request receiving unit (communication unit 42) configured to receive a communication request (call request, interruption request, etc.) from any one of the ophthalmic examination apparatus, the internal examiner terminal, and the external examiner terminal. Further, the communication establishment unit may include a selection unit (412) configured to, based on the communication request received by the communication request receiving unit, select one or more apparatuses other than the apparatus which has sent the communication request from among the ophthalmic examination apparatus, the internal examiner terminal, and the external examiner terminal. In this case, the communication establishment unit can establish communication between the apparatus which has sent the communication request and the one or more apparatuses selected by the selection unit.

According to such a configuration, in response to a call request, an interruption request, or the like from any one of the ophthalmic examination apparatus, the internal examiner terminal, and the external examiner terminal, it is possible to establish communication between the apparatus which has sent the communication request and another apparatus. For example, it is possible to select an internal examiner or an external examiner according to a request for assistance from the subject, and to assign the selected examiner in charge of assisting the subject. In addition, an internal examiner or an external examiner can offer to give support based on the state of the examination, the support situation by other examiners, or the like.

The ophthalmic examination system of the embodiment may include one or more internal examiner terminals and one or more external examiner terminals. In particular, a plurality of internal examiner terminals and a plurality of external examiner terminals may be included. Further, the communication establishment unit of the management apparatus may include a storage unit (411) in which attribute information is stored in advance. The attribute information includes any part or all of the followings: attributes of at least one internal examiner terminal; attributes of at least one internal examiner; attributes of at least one external examiner terminal; and attributes of at least one external examiner. In addition, the communication request may include information on such attributes. Based on the communication request received by the communication request receiving unit and the attribute information, the selection unit can select at least one apparatus from the one or more internal examiner terminals and the one or more external examiner terminals.

According to such a configuration, it is possible to select an examiner having the attributes conforming to the state of the subject, the state of examination, or the like, and to assign the selected examiner to assist the subject. When examiner terminals and examiners are always associated in one-to-one correspondence, it is possible to equate the attributes of the examiner terminals and the attributes of the examiners. In the absence of such a one-to-one correspondence, an examiner terminal and an examiner can be associated with each other by the use of examiner ID input by the examiner at the time of using the examiner terminal, so that it is possible to make the above selection using this association.

In an embodiment, the ophthalmic examination apparatus may include an examination state information generating unit (22a), a communication request generating unit (22b), and a communication request sending unit (communication unit 24). The examination state information generating unit is configured to generate the examination state information indicating the state of the examination performed with the ophthalmic examination apparatus. The communication request generating unit is configured to generate the communication request described above based on the examination state information generated by the examination state information generating unit. The communication request sending unit is configured to send the communication request generated by the communication request generating unit to the management apparatus.

According to such a configuration, it is possible to automatically generate a communication request according to the state of the subject, the state of the examination, or the like, and to transmit the communication request to the management apparatus, so that the assist can be promptly started. Also, the possibility of missing the subject who needs assistance is reduced.

In the embodiment, each of the ophthalmic examination apparatus, the internal examiner terminal, and the external examiner terminal may include a user interface (UI: for example, an operation unit, an audio input unit, etc.) configured to receive instructions to send a communication request to the management apparatus.

With such a configuration, the subject and the examiner can send a communication request at a desired timing.

In the embodiment, when the communication request receiving unit of the management apparatus receives a communication request from the ophthalmic examination apparatus, the selection unit can determine whether or not the communication of one of the internal examination terminal and the external examination terminal which corresponds to the communication request is actually established. Examples of apparatuses which corresponds to the communication request includes an internal examination terminal that is used in the facility in which the ophthalmic examination apparatus is installed, an internal examination terminal (internal examiner) and an external examination terminal (external examiner) having predetermined attributes, and the like.

When it is determined that the communication of the one apparatus (i.e., the internal examination terminal or the external examination terminal) is not actually established (that is, when it is determined that the communication between the one apparatus and the ophthalmic examination apparatus or the like is not currently established, in other words, when it is determined that assistance is not currently given using the one apparatus), the selection unit selects the one apparatus (i.e., the internal examination terminal or the external examination terminal). With such processing, communication between the one apparatus (i.e., the internal examination terminal or the external examination terminal) and the ophthalmic examination apparatus is established.

On the contrary, when it is determined that the communication of the one apparatus (i.e., the internal examination terminal or the external examination terminal) has already been established (that is, when it is determined that the communication between the one apparatus and the ophthalmic examination apparatus or the like is currently being established, in other words, when it is determined that assistance is currently given using the one apparatus), the selection unit selects the other apparatus (i.e., the external examination terminal or the internal examination terminal). With such processing, communication between the other apparatus (i.e., the external examination terminal or the internal examination terminal) and the ophthalmic examination apparatus is established.

According to such a configuration, when an assist request is issued from the subject while an internal examiner in the facility is supporting another subject, the assist request is sent to an external examiner. Conversely, if an appropriate external examiner is supporting another subject, the assist request is sent to an internal examiner. Thereby, the assist can be promptly started.

It is also conceivable that both the internal examiner and the external examiner are assisting other subjects. In this case, for example, a message indicating that it will take time until the assist will be given can be presented to the subject, and a message indicating that there is a subject waiting assistance can be presented to the internal examiner and/or the external examiner.

In an embodiment, the management apparatus may include an information transmission unit (transfer controller 402, communication unit 42, etc.) configured to transmit at least part of information communicated between the ophthalmic examination apparatus and one apparatus of the internal examiner terminals and the external examiner terminals, to the other apparatus of the internal examiner terminals and the external examiner terminals. In this case, the display controller (controller) of the other apparatus can control the display to display the information transmitted by the information transmission unit.

According to such a configuration, it is possible for an examiner to perceive the contents of communication between the subject and another examiner. As a result, additional assistance and training can be performed in a suitable manner.

In an embodiment, the management apparatus may include an information transmission unit (transfer controller 402, communication unit 42, etc.) configured to transmit information representing the current state of communication (communication mode) established by the communication establishment unit to at least one of the internal examiner terminal and the external examiner terminal. In this case, the display controller (controller) of the apparatus that has received the information can control the display to display the information.

With such a configuration, it is possible for the internal examiner and the external examiner to perceive what kind of assistance is being performed to the ophthalmic examination apparatus. As a result, additional assistance and training can be performed in a suitable manner.

In an embodiment, the ophthalmic examination apparatus may include a visual target presentation unit (examination unit 21) configured to present a visual target to the subject's eye for visual acuity test, and an information transmission unit (communication unit 24) configured to transmit information indicating the visual target presented by the visual target presentation unit to the management apparatus. In this case, the information transfer unit of the management apparatus can transfer the information transmitted by the information transmission unit to at least one of the internal examiner terminal and the external examiner terminal. The display controller (controller) of the apparatus that has received the transferred information can control the display to display the visual target being presented to the subject's eye based on the received information. With such processing, for example, the visual target currently presented to the subject's eyes is displayed in the presentation information display areas 1010L and 1010R of FIG. 10.

According to such a configuration, the internal examiner and the external examiner can easily perceive the visual target currently presented to the subject's eye, so it is possible to appropriately assist the visual acuity test. In particular, the external examiner can appropriately perform assist from a remote place.

In an embodiment, the display controller can control the display to display a graphical user interface (GUI displayed in the presentation information operation area 1050, or the like) for selecting the visual target. In this case, the apparatus that has received the information transfer from the management apparatus may include an information transmission unit (communication unit) configured to transmit information indicating the visual target selected by the use of the graphical user interface to the management apparatus. Further, the information transfer unit of the management apparatus transfers the information transmitted by the information transmission unit of this apparatus to the ophthalmic examination apparatus. The visual target presentation unit of the ophthalmic examination apparatus presents visual targets to the subject's eye based on the information transferred by the information transfer unit of the management apparatus.

With such a configuration, it is possible to select and change the visual target presented to the subject's eye using the internal examiner terminal or the external examiner terminal.

In order to train an examiner (for example, internal examiner), the contents of the support actually performed can be recorded. For example, the ophthalmic examination system may be configured to record a history of information exchanged between an examiner and a subject, to perform picture recording (for example, to record a moving image) of an examiner providing support and/or a subject receiving support, or the like.

The management server 4 of an embodiment functions as an example of the ophthalmic examination management server of the present invention. In general, an ophthalmic examination management server of an embodiment (management server 4) includes a communication unit (42), a communication establishment unit (41), and an information transfer unit (transfer controller 402, communication unit 42, etc.). The communication unit includes a configuration for communicating via the communication line (N) with each of the ophthalmic examination apparatus (2), the internal examiner terminal (3) used by an internal examiner at the facility where the ophthalmic examination apparatus is installed, and the external examiner terminal used by an external examiner outside the facility. The communication establishment unit is configured to be able to establish communication between at least two apparatuses selected from the ophthalmic examination apparatus, the internal examiner terminal, and the external examiner terminal. The information transfer unit transfers the information transmitted from one of the at least two apparatuses whose communication has been established by the communication establishment unit to another apparatus.

According to such an ophthalmic examination management server, like the ophthalmic examination system of the embodiment, it is possible to cope with various situations arising in the remote examination. The ophthalmic examination management server according to the embodiment may include any of the configurations described in the ophthalmic examination system of the embodiment.

The embodiments described above are mere examples for embodying or carrying out the present invention, and therefore susceptible to several modifications and variations (omission, substitution, addition, etc.), all coming within the scope of the invention.

What is claimed is:

1. An ophthalmic examination system comprising:
    an ophthalmic examination apparatus;
    an internal examiner terminal used by an internal examiner in a facility where the ophthalmic examination apparatus is installed, the internal examiner terminal configured to receive information concerning an ophthalmic examination of a subject from the ophthalmic examination apparatus;
    an external examiner terminal used by an external examiner outside the facility;
    communication establishment circuitry configured to establish communication between the ophthalmic examination apparatus and a selected at least one of the external examiner terminal and the internal examiner terminal based on a selected communication mode selected from a plurality of predetermined communication modes that control a communication state of the internal examiner terminal and the external examiner terminal; and
    communication request receiving circuitry configured to receive a communication request from the ophthalmic examination apparatus, wherein
    the communication establishment circuitry selects one of the plurality of predetermined communication modes based on the communication request, and establishes the communication between the ophthalmic examination apparatus and the selected at least one of the external examiner terminal and the internal examiner terminal based on the selected one of the plurality of predetermined communication modes and the communication request, the plurality of predetermined communication modes include a second mode in which the subject is receiving assistance from the external examiner terminal, a third mode in which the subject is receiving assistance from the internal examiner terminal, and a fourth mode in which the subject is receiving assistance from the internal examiner terminal and the external examiner terminal, each of the plurality of predetermined communication modes having a unique identifier,
    the communication including a transmission, from the ophthalmic examination apparatus to the selected at least one of the internal examiner terminal and the external examiner terminal, of the information concerning the ophthalmic examination of the subject, and
    the ophthalmic examination apparatus includes
        examination state information generating circuitry configured to generate examination state information representing a completed phase of the ophthalmic examination,
        communication request generating circuitry configured to generate the communication request based on the examination state information generated by the examination state information generating circuitry, and
        communication request sending circuitry configured to send the communication request generated by the communication request generating circuitry to a management apparatus.

2. The ophthalmic examination system according to claim 1, wherein the information concerning the ophthalmic examination of the subject includes a copy of communications made between the subject and the internal examiner.

3. The ophthalmic examination system according to claim 1, wherein the information concerning the ophthalmic examination of the subject includes information from which a state of the subject and a state of the ophthalmic examination of the subject may be determined.

4. The ophthalmic examination system of claim 1, wherein each of the ophthalmic examination apparatus, the internal examiner terminal, and the external examiner terminal includes a user interface configured to receive an instruction for sending the communication request to the management apparatus.

5. The ophthalmic examination system of claim 1, further comprising:
the management apparatus includes information transmission circuitry configured to send at least part of information communicated between the ophthalmic examination apparatus and one apparatus of the internal examiner terminal and the external examiner terminal, to another apparatus; and
the other apparatus includes a display, and a display controller configured to display information sent by the information transmission circuitry on the display.

6. The ophthalmic examination system of claim 1, further comprising:
the management apparatus includes information transmission circuitry configured to send information representing current communication establishment state by the communication establishment circuitry to at least one apparatus of the internal examiner terminal and the external examiner; and
the at least one apparatus includes a display, and a display controller configured to display information sent by the information transmission circuitry on the display.

7. The ophthalmic examination system of claim 1, wherein
the ophthalmic examination apparatus comprises:
visual target presentation circuitry configured to present visual targets for visual acuity test to a subject's eye; and
information transmission circuitry configured to send, to the management apparatus, information indicating a visual target being presented by the visual target presentation circuitry,
information transfer circuitry of the management apparatus transfers information sent from the information transmission circuitry to at least one apparatus of the internal examiner terminal and the external examiner terminal, and
the at least one apparatus includes a display, and a display controller configured to display the visual target being presented to the subject's eye on the display based on the information transferred by the information transfer circuitry.

8. The ophthalmic examination system of claim 7, wherein
the display controller displays graphical user interface for selecting visual targets on the display,
the at least one apparatus includes an information transmission circuitry configured to send information indicating a visual target selected by the graphical user interface to the management apparatus,
the information transfer circuitry of the management apparatus transfers information sent by the information transmission circuitry to the ophthalmic examination apparatus, and
the visual target presentation circuitry of the ophthalmic examination apparatus presents a visual target to the subject's eye based on the information transferred by the information transfer circuitry.

9. The ophthalmic examination system of claim 1, wherein the ophthalmic examination apparatus comprises:
an examination optical system comprising an optical element to be applied to a subject's eye, and a projection system configured to project an examination light beam for examining the subject's eye via the optical element onto the subject's eye;
an information presenting optical system comprising a display, and a light guide system configured to guide a display light beam output from the display via the optical element to the subject's eye; and
a controller configured to display information sent from the internal examiner terminal or the external examiner terminal on the display.

10. The ophthalmic examination system according to claim 1, wherein the examination state information further includes an interim report of the ophthalmic examination, an elapsed time of the ophthalmic examination, and a history of visual targets that have been presented in the ophthalmic examination.

11. The ophthalmic examination system according to claim 1, wherein the external examiner terminal includes a display configured to display
the identifier of the selected communication mode selected from the plurality of predetermined communication modes by the communication establishment circuitry, and
a time at which the communication was established according to the selected communication mode.

12. An ophthalmic examination method comprising:
performing an ophthalmic examination of an eye of a subject with an ophthalmic examination apparatus;
receiving, by a selected at least one of an internal examiner terminal and an external examiner terminal, information concerning the ophthalmic examination of the eye of the subject from the ophthalmic examination apparatus, the internal examiner terminal being used by an internal examiner in a facility where the ophthalmic examination apparatus is installed and the external examiner terminal being used by an external examiner in another facility where the ophthalmic examination apparatus is not installed, the selected at least one of the internal examiner terminal and the external examiner terminal being selected based on a selected communication mode selected from a plurality of predetermined communication modes that control a current communication state of the internal examiner terminal and the external examiner terminal;
selecting one of the plurality of predetermined communication modes based on the communication request;
establishing communication, by a communication establishment circuitry, between the ophthalmic examination apparatus and the selected at least one of the internal examiner terminal and the external examiner terminal; and
receiving, by a communication request receiving circuitry, a communication request from the ophthalmic examination apparatus;
establishing, by the communication establishment circuitry, the communication between the ophthalmic examination apparatus and the selected at least one of the internal examiner terminal and the external examiner terminal based on the selected one of the plurality of predetermined communication modes and the communication request, the plurality of predetermined communication modes include a second mode in which the subject is receiving assistance from the external examiner terminal, a third mode in which the subject is receiving assistance from the internal examiner terminal, and a fourth mode in which the subject is receiving assistance from the internal examiner terminal and the external examiner terminal, each of the plurality of predetermined communication modes having a unique identifier;

transmitting, as the communication, the information concerning the ophthalmic examination of the subject, from the ophthalmic examination apparatus to the selected at least one of the internal examiner terminal and the external examiner terminal;

generating examination state information representing a completed phase of the ophthalmic examination;

generating the communication request based on the examination state information generated by the examination state information generating circuitry; and sending the communication request generated by the communication request generating circuitry to a management apparatus.

* * * * *